(12) United States Patent
Remmereit

(10) Patent No.: US 10,259,833 B2
(45) Date of Patent: Apr. 16, 2019

(54) NATURAL LIPIDS CONTAINING NON-OXIDIZABLE FATTY ACIDS

(71) Applicant: Bergen Teknologioverføring AS, Bergen (NO)

(72) Inventor: Jan Remmereit, Hovdebygda (NO)

(73) Assignee: Bergen Teknologioverføring AS, Bergen (NO)

( * ) Notice: Subject to any disclaimer, the term of this patent is extended or adjusted under 35 U.S.C. 154(b) by 0 days.

(21) Appl. No.: 15/725,431

(22) Filed: Oct. 5, 2017

(65) Prior Publication Data

US 2018/0030073 A1    Feb. 1, 2018

Related U.S. Application Data

(63) Continuation of application No. 14/774,434, filed as application No. PCT/IB2014/001254 on Mar. 10, 2014, now abandoned.

(60) Provisional application No. 61/775,834, filed on Mar. 11, 2013.

(51) Int. Cl.

| | |
|---|---|
| C07F 9/06 | (2006.01) |
| A61K 45/06 | (2006.01) |
| A61K 31/19 | (2006.01) |
| A61K 31/202 | (2006.01) |
| A61K 31/23 | (2006.01) |
| A61K 31/232 | (2006.01) |
| A61K 31/683 | (2006.01) |
| A61K 31/685 | (2006.01) |
| A61K 35/74 | (2015.01) |
| C07F 9/655 | (2006.01) |
| C07F 9/10 | (2006.01) |
| A61K 8/36 | (2006.01) |
| A61K 8/37 | (2006.01) |
| A61Q 19/00 | (2006.01) |
| A61Q 19/06 | (2006.01) |
| A61K 8/92 | (2006.01) |
| A23L 33/00 | (2016.01) |
| A23L 33/115 | (2016.01) |
| A23K 20/158 | (2016.01) |
| C11B 1/10 | (2006.01) |
| A61K 9/00 | (2006.01) |
| A61K 47/24 | (2006.01) |

(52) U.S. Cl.
CPC ............ *C07F 9/062* (2013.01); *A23K 20/158* (2016.05); *A23L 33/115* (2016.08); *A23L 33/30* (2016.08); *A61K 8/361* (2013.01); *A61K 8/37* (2013.01); *A61K 8/925* (2013.01); *A61K 31/19* (2013.01); *A61K 31/202* (2013.01); *A61K 31/23* (2013.01); *A61K 31/232* (2013.01); *A61K 31/683* (2013.01); *A61K 31/685* (2013.01); *A61K 35/74* (2013.01); *A61K 45/06* (2013.01); *A61Q 19/00* (2013.01); *A61Q 19/06* (2013.01); *C07F 9/106* (2013.01); *C07F 9/6552* (2013.01); *C11B 1/10* (2013.01); *A23V 2002/00* (2013.01); *A61K 9/0014* (2013.01); *A61K 9/0019* (2013.01); *A61K 47/24* (2013.01); *A61K 2800/10* (2013.01)

(58) Field of Classification Search
CPC .... A61K 31/19; A61K 31/202; A61K 31/232; A61K 31/683; A61K 31/685; A61K 31/23; A61K 35/74; A61K 8/361; A61K 8/37; A61K 8/814; A61K 47/24; A23V 2002/00; A23V 2250/1942; A23K 20/158; A23L 33/115; A23L 33/30; C12N 1/12; C07F 9/062; C07F 9/106; C07F 9/6552

See application file for complete search history.

(56) References Cited

U.S. PATENT DOCUMENTS

2001/0046691 A1 * 11/2001 Bailey ................. A23D 9/00
435/134

FOREIGN PATENT DOCUMENTS

| CA | 2689724 | 12/2008 | |
|---|---|---|---|
| CN | 101010101 | 8/2007 | |
| JP | 58038215 | 3/1983 | |
| WO | 2004/000854 | 12/2003 | |
| WO | 2006/009464 | 1/2006 | |
| WO | WO-2011097261 A1 * | 8/2011 | ........... C07K 14/405 |

OTHER PUBLICATIONS

Jorgensen et. al., Journal of Medicinal Chemistry, 2009, American Chemical Society, vol. 52, pp. 1172-1179 (Year: 2009).*
International Search Report and Written Opinion, International Patent Application No. PCT/IB2014/001254, dated Feb. 9, 2015.
Imuthes: "TMI-100 Series (CVD)" Mar. 1, 2013, pp. 1-8, retrieved from the internet: URL: http://wayback.archive.org/web/20130301014904/http://www.imuthes.com/products/pipeline/timi-100-series-cvd.
Moya-Falcon et al. "Phospholipid molecular species, beta-oxidation, desaturation and elongation of fatty acids in Atlantic salmon hepatocytes: Effects of temperature and 3-thia fatty acids", Comparative Biochemistry and Physiology. Part B, vol. 145, No. 1, Sep. 2006, pp. 68-80.
Gidden et al. "Lipid Compositions in *Escherichia coli* and Bacillus subtilis During Growth as Determined by MALDI-TOF and TOF/TOF Mass Spectrometry" Int. J. Mass Spectrom, 283(1-3), p. 178-184, Jun. 2009.

* cited by examiner

*Primary Examiner* — Sarah Pihonak
(74) *Attorney, Agent, or Firm* — Casimir Jones S.C.; J. Mitchell Jones

(57) ABSTRACT

Provided herein is technology relating to natural lipids containing non-β-oxidizable fatty acids and particularly, but not exclusively, to compositions and methods related to the production and use of natural lipids containing non-β-oxidizable fatty acids.

9 Claims, No Drawings

NATURAL LIPIDS CONTAINING NON-OXIDIZABLE FATTY ACIDS

CROSS-REFERENCE TO RELATED APPLICATIONS

The present application is a continuation of U.S. patent application Ser. No. 14/774,434, filed Sep. 10, 2015, which is a 371 U.S. National Phase Entry of International Application No. PCT/IB2014/001254, filed Mar. 10, 2014, which claims priority to U.S. Provisional Patent Application No. 61/775,834, filed Mar. 11, 2013, the contents of which are incorporated by reference in their entireties.

FIELD OF TECHNOLOGY

Provided herein is technology relating to natural lipids containing non-β-oxidizable fatty acids and particularly, but not exclusively, to compositions and methods related to the production and use of natural lipids containing non-β-oxidizable fatty acids.

BACKGROUND

By introducing particular atoms into a fatty acid, fatty acid analogues are produced that are not catabolized by β-oxidation. For example, European Patent Specification No. 0345038 described the preparation of non-β-oxidizable fatty acid analogues having the general formula

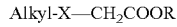

wherein Alkyl represents a saturated or unsaturated hydrocarbon group of from 8 to 22 carbon atoms; X represents O, S, SO, and $SO_2$; and R represents hydrogen or a $C_1$-$C_4$ alkyl. Subsequently, PCT/NO99/00135, PCT/NO99/00136, and PCT/NO99/00149 described similar non-β-oxidizable fatty acid analogues having the formula

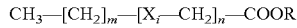

wherein n is an integer from 1 to 12; m is an integer from 0 to 23; i is an odd number that indicates the position of $X_i$ relative to COOR; $X_i$ are independently selected from the group comprising O, S, SO, $SO_2$, Se, and $CH_2$; and R represents hydrogen or $C_1$-$C_4$ alkyl; with the proviso that at least one of the $X_i$ is not $CH_2$. As indicated by these two formulae, these compounds comprise one or several X groups (e.g., selenium or sulfur) at positions 3, 5, 7, 9, etc.

Due to the X atom (e.g., sulfur or selenium) that is substituted in the carbon chain of these fatty acid analogues, the compounds are not β-oxidized in the mitochondria beyond the position of the X atom. Thus, the degradation of these molecules must start from the methyl end of the fatty acid, which is a rather slow metabolic process. As such, the catabolism of these fatty acid analogues includes ω-oxidation and chain shortening of the dicarboxylic acid by peroxisomes. Enzymes in the endoplasmic reticulum ω-hydroxylate and further oxidize the hydroxylated fatty acid to a dicarboxylic acid. This acid may then be chain shortened by β-oxidation in the peroxisomes.

These substituted analogues have been demonstrated to have general antioxidant properties due to the presence of the heteroatom (see, e.g., WO/1997/03663). In addition, the biochemical characteristics of non-β-oxidizable fatty acid analogues provide particular beneficial activities, for example, to treat and/or prevent obesity (NO 2000 5461); diabetes (NO 2000 5462); primary and secondary stenosis (NO 2000 5463); cancer (NO 2002 5930); proliferate skin disorders (NO 2003 1080); and inflammatory and autoimmune disorders (NO 2003 2054). See also Int'l App. Nos. WO/1999/058123, WO/2001/NO00301, WO/2001/NO00393, and WO/2001/NO00470; U.S. Pat. Nos. 6,365,628; 6,441,036; 6,417,232; and 7,026,356; and U.S. Pat. App. Pub. No. 2002198259.

Additional work described synthetic phospholipid compounds containing non-β-oxidizable fatty acid analogues. (see, e.g., U.S. Pat. No. 8,178,713). These phospholipids (e.g., phosphatidylcholine and triacylglycerol compounds) increased fatty acid oxidation and decreased hepatic lipid levels in vivo. Due to similarities in molecular structure with the fatty acid analogues from which they are synthesized, these phospholipids are anticipated to have similar biological activities as the fatty acid analogues, e.g., as agents to treat hyperinsulinemia, hyperglycemia, fatty liver, and obesity. However, the in vitro synthesis of these lipid compounds lacks efficiency. Moreover, the synthetic phospholipid preparations may contain non-natural substances that are not desirable or appropriate for administration to a subject.

SUMMARY

As such, provided herein is technology related to producing natural phospholipids in an in vivo system. In particular, embodiments of the technology relate to providing a non-β-oxidizable fatty acid analogue as a nutrient to a living organism (e.g., a yeast, a bacterium, an alga, an archaeon, etc.) that produces a phospholipid incorporating the non-β-oxidizable fatty acid analogue and then isolating the phospholipid containing the non-β-oxidizable fatty acid analogue from the living organism. The technology also encompasses embodiments related to compositions comprising a phospholipid incorporating the non-β-oxidizable fatty acid analogue and uses of such compositions.

In some embodiments, the present invention provides composition comprising a natural lipid and a natural biomolecule, wherein the natural lipid comprises a non-beta-oxidizable fatty acid analogue. In some embodiments, the natural biomolecule is a second lipid. In some embodiments, the composition comprises an oil, powder, crystal, wax, emulsion, micelle, vesicle, or film. In some embodiments, the non-beta-oxidizable fatty acid analogue is tetradecylthioacetic acid (TTA). In some embodiments, the non-beta-oxidizable fatty acid analogue is tetradecylselenoacetic acid (TSA). In some embodiments, the natural lipid is a phospholipid. In some embodiments, the natural lipid comprises a phosphatidylcholine, phosphatidylethanolamine, phosphatidylserine, phosphatidylglycerol, or phosphatidylinositol headgroup. In some embodiments, the natural lipid comprises an ether link between a lipid tail and a headgroup. In some embodiments, the natural lipid has a biological activity in a mammal. In some embodiments, the biomolecule has a biological activity in a mammal. In some embodiments, the natural lipid is a sphingolipid. In some embodiments, the biomolecule is a protein, nucleic acid, steroid, cofactor, or vitamin. In some embodiments, the natural lipid is an omega-3 fatty acid moiety. In some embodiments, the omega-3 fatty acid moiety is selected from the group consisting of EPA and DHA. In some embodiments, the natural lipid is an omega-6 fatty acid moiety. In some embodiments, the natural lipid is a conjugated linoleic acid moiety.

In some embodiments, the present invention provides a composition comprising a natural lipid, the composition obtainable by a process comprising the steps of: 1) providing a biologically active biomolecule to a living organism in vitro; and 2) isolating the composition comprising the natural lipid from the living organism. In some embodiments, the biologically active biomolecule is a non-beta-oxidizable fatty acid analogue. In some embodiments, the biologically active biomolecule is TTA or a furan fatty acid. In some embodiments, the lipid comprises a non-beta-oxidizable fatty acid analogue. In some embodiments, the lipid comprises TTA or a furan fatty acid. In some embodiments, the living organism is an alga. In some embodiments, the living organism is a bacterium or an archaeon. In some embodiments, the living organism is a yeast. In some embodiments, the process further comprises producing an extract, fraction, or composition comprising the biologically active molecule from a second living organism. In some embodiments, the process further comprises producing an extract, fraction, or composition comprising the biologically active molecule from a marine organism. In some embodiments, the compositions further comprise a second biomolecule. In some embodiments, the second biomolecule is a lipid, protein, nucleic acid, steroid, cofactor, or vitamin. In some embodiments, the living organism is in a culture. In some embodiments, the culture comprises a plurality of living organisms, wherein each living organism is characterized by a type and the culture comprises a plurality of the types. In some embodiments, the type is a species, subspecies, isolate, clone, genus, family, division, kingdom, or other taxonomic classification. In some embodiments, the living organism is a thermophile. In some embodiments, the second living organism is a thermophile. In some embodiments, the TTA is produced by reacting thioglycolic acid with bromotetradecane. In some embodiments, the TTA is produced by a method comprising dissolving sodium hydroxide in methanol to produce a reaction solution, adding thioglycolic acid to the reaction solution, adding 1-bromotetradecane to the reaction solution, adding citric acid to the reaction solution, and isolating TTA from the reaction solution. In some embodiments, the composition comprises an oil, powder, crystal, wax, emulsion, micelle, vesicle, or film. In some embodiments, the natural lipid is a phospholipid. In some embodiments, the natural lipid comprises a phosphatidylcholine, phosphatidylethanolamine, phosphatidylserine, phosphatidylglycerol, or phosphatidylinositol headgroup. In some embodiments, the natural lipid comprises an ether link between a lipid tail and a headgroup. In some embodiments, the natural lipid has a biological activity in a mammal. In some embodiments, the second biomolecule has a biological activity in a mammal. In some embodiments, the natural lipid is a sphingolipid. In some embodiments, the natural lipid further comprises an omega-3 fatty acid moiety. In some embodiments, the omega-3 fatty acid moiety is selected from the group consisting of EPA and DHA. In some embodiments, the natural lipid further comprises an omega-6 fatty acid moiety. In some embodiments, the natural lipid further comprises a conjugated linoleic acid moiety.

In some embodiments, the present invention provides methods for producing a composition comprising a natural lipid, the method comprising: 1) providing a biologically active biomolecule to a living organism in vitro; and 2) isolating the composition comprising the natural lipid from the living organism. In some embodiments, the biologically active biomolecule is a non-beta-oxidizable fatty acid analogue. In some embodiments, the biologically active biomolecule is TTA. In some embodiments, the natural lipid comprises a non-beta-oxidizable fatty acid analogue. In some embodiments, the natural lipid comprises TTA. In some embodiments, the living organism is an alga. In some embodiments, the living organism is a bacterium or an archaeon. In some embodiments, the living organism is a yeast. In some embodiments, the method further comprises producing an extract, fraction, or composition comprising the biologically active molecule from a second living organism. In some embodiments, the method further comprise producing an extract, fraction, or composition comprising the biologically active molecule from a marine organism. In some embodiments, the composition comprising the natural lipid further comprises a second biomolecule. In some embodiments, the second biomolecule is a lipid, protein, nucleic acid, steroid, cofactor, or vitamin. In some embodiments, the living organism is in a culture. In some embodiments, the culture comprises a plurality of living organisms, wherein each living organism is characterized by a type and the culture comprises a plurality of the types. In some embodiments, the type is a species, subspecies, isolate, clone, genus, family, division, kingdom, or other taxonomic classification. In some embodiments, the living organism is a thermophile. In some embodiments, the second living organism is a thermophile. In some embodiments, the TTA is produced by reacting thioglycolic acid with bromotetradecane. In some embodiments, the TTA is produced by a method comprising dissolving sodium hydroxide in methanol to produce a reaction solution, adding thioglycolic acid to the reaction solution, adding 1-bromotetradecane to the reaction solution, adding citric acid to the reaction solution, and isolating TTA from the reaction solution. In some embodiments, the composition comprises an oil, powder, crystal, wax, emulsion, micelle, vesicle, or film. In some embodiments, the natural lipid is a phospholipid. In some embodiments, the natural lipid comprises a phosphatidylcholine, phosphatidylethanolamine, phosphatidylserine, phosphatidylglycerol, or phosphatidylinositol headgroup. In some embodiments, the natural lipid comprises an ether link between a lipid tail and a headgroup. In some embodiments, natural lipid has a biological activity in a mammal. In some embodiments, the biomolecule has a biological activity in a mammal. In some embodiments, the natural lipid is a sphingolipid. In some embodiments, the methods further comprise
testing the composition comprising the natural lipid in a mouse model of a metabolic disease. In some embodiments, the natural lipid further comprises an omega-3 fatty acid moiety. In some embodiments, the omega-3 fatty acid moiety is selected from the group consisting of EPA and DHA. In some embodiments, the natural lipid further comprises an omega-6 fatty acid moiety. In some embodiments, the natural lipid further comprises a conjugated linoleic acid moiety.

In some embodiments, the present invention provides structured phospholipid compositions comprising phospholipid molecules of the following structure:

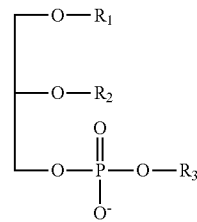

wherein one of R1 and R2 is a non-beta-oxidizable fatty acid analogue moiety and the other of R1 and R2 is a bioactive fatty acid moiety selected from the group consisting of an omega-3 fatty acid moiety, on omega-6 fatty acid moiety, a polyunsaturated fatty acid moiety, a conjugated linoleic fatty acid moiety, and combinations thereof. In some embodiments, the composition comprises greater than 10%, 20%, 30%, 40%, 50%, 80%, 90% or 99% on a molar basis of the non-beta-oxidizable fatty acid analogue moiety at position R1. In some embodiments, the composition comprises greater than 50%, 80%, 90% or 99% on a molar basis of the non-beta-oxidizable fatty acid analogue moiety at position R2. In some embodiments, the composition comprises greater than about 50%, 80%, 90% or 99% on a molar basis of the bioactive fatty acid moieties or combinations thereof at position R2. In some embodiments, the composition comprises greater than about 50%, 80%, 90% or 99% on a molar basis of the bioactive fatty acid moiety at position R1. In some embodiments, the bioactive fatty acid moiety is selected from the group consisting of EPA, DHA and a combination thereof. In some embodiments, the bioactive fatty acid moiety is EPA. In some embodiments, the bioactive fatty acid moiety is DHA. In some embodiments, the bioactive fatty acid moiety is conjugated linoleic acid.

In some embodiments, the present invention provides for the use of a composition comprising a natural lipid and a natural biomolecule or a structured phospholipid, wherein the lipid or structured phospholipid comprises a non-beta-oxidizable fatty acid analogue, for the preparation of a medicament.

In some embodiments, the present invention provides for the use of a composition comprising a natural lipid and a natural biomolecule or a structured phospholipid, wherein the lipid or structured phospholipid comprises a non-beta-oxidizable fatty acid analogue, for the preparation of a food product. In some embodiments, the food product has a biological activity in a human In some embodiments, the present invention provides for the use of a composition for ameliorating a metabolic disease in a subject, the composition comprising a natural lipid and a natural biomolecule or a structured phospholipid, wherein the lipid or structured phospholipid comprises a non-beta-oxidizable fatty acid analogue or a furan fatty acid. In some embodiments, the non-beta-oxidizable fatty acid analogue is TTA.

In some embodiments, the present invention provides for the use of a composition comprising a lipid and a natural biomolecule or a structured phospholipid, wherein the lipid or structured phospholipid comprises a non-beta-oxidizable fatty acid analogue, for the preparation of a medicament to treat a disease. In some embodiments, the disease is a metabolic disease. In some embodiments, the metabolic disease is obesity, diabetes, hypercholesterolemia, hyperlipidemia, glucose intolerance, aberrant adipose tissue storage and/or distribution, syndrome X, hypertension, fatty liver, hyperglycemia, hyperinsulinemia, or stenosis. In some embodiments, the disease is cancer, vascular disease, skin condition, or an inflammatory disorder.

In some embodiments, the present invention provides a combination comprising a liposome and a composition as described above.

In some embodiments, a cosmetic formulation comprising a lipid composition as described above.

In some embodiments, the present invention provides methods of treating a condition chosen from syndrome X, obesity or an overweight condition, hypertension, fatty liver, diabetes, hyperglycaemia, hyperinsulinemia, insulin resistance, hyperlipidemia, hypercholesterolemia, hypertriglyceridemia (HTG), and stenosis, comprising administering to a subject in need thereof an effective amount of a composition as described above, or a pharmaceutically acceptable salt thereof. In some embodiments, the method provides for producing weight loss or a reduction of fat mass in a human or non-human animal in need thereof.

In some embodiments, the present invention provides methods for the treatment of inflammatory disorders, comprising administering to a subject in need thereof an effective amount of a composition as described above, or a pharmaceutically acceptable salt thereof.

In some embodiments, the present invention provides methods of lowering concentration of cholesterol and triglycerides in the blood of mammals and/or inhibiting the oxidative modification of low density lipoprotein, comprising administering to a subject in need thereof an effective amount of a composition as described above, or a pharmaceutically acceptable salt thereof.

In some embodiments, the present invention provides methods for producing weight loss or a reduction of the fat mass in a human or non-human animal in need thereof, comprising administering thereto an effective amount of a composition as described above, or a pharmaceutically acceptable salt thereof.

In some embodiments, the present invention provides methods for the modification of the fat distribution and content of animals, comprising administering to a subject in need thereof an effective amount of a composition as described above, or a pharmaceutically acceptable salt thereof.

In some embodiments, the present invention provides methods of inhibiting the growth of tumors, comprising administering to a subject in need thereof an effective amount of a composition as described above, or a pharmaceutically acceptable salt thereof.

In some embodiments, the present invention provides methods for the treatment or inhibition of primary and secondary metastatic neoplasms, comprising administering to a subject in need thereof an effective amount of a composition as described above, or a pharmaceutically acceptable salt thereof.

In some embodiments, the present invention provides methods for the treatment of proliferative skin disorders, comprising administering to a subject in need thereof an effective amount of a composition as described above, or a pharmaceutically acceptable salt thereof.

In some embodiments, the present invention provides methods for the inhibition of proliferation or induction of differentiation of keratinocytes, comprising administering to a subject in need thereof an effective amount of a composition as described above, or a pharmaceutically acceptable salt thereof.

In some embodiments, the present invention provides methods for the treatment of inflammatory disorders, comprising administering to a subject in need thereof an effective amount of a composition as described above, or a pharmaceutically acceptable salt thereof.

In some embodiments, the present invention provides methods for enhancing the endogenous production of interleukin-10 (IL-10) in mammalian cells or tissues, comprising administering to a subject in need thereof an effective amount of a composition as described above, or a pharmaceutically acceptable salt thereof.

In some embodiments, the present invention provides methods for suppression of the endogenous production of interleukin-2 (IL-2) in mammalian cells or tissues, comprising administering to a subject in need thereof an effective amount of a composition as described above, or a pharmaceutically acceptable salt thereof.

In some embodiments, the present invention provides methods for the inhibition of proliferation of stimulated peripheral mononuclear cells (PBMC), comprising administering to a subject in need thereof an effective amount of a composition as described above, or a pharmaceutically acceptable salt thereof.

In some embodiments, the present invention provides a pharmaceutical composition comprising a natural lipid as described above, a natural biomolecule, and a pharmaceutically acceptable carrier. In some embodiments, the present invention provides a pharmaceutical composition comprising a structured phospholipid as described above. In some embodiments, the natural lipid comprises TTA or a furan fatty acid. In some embodiments, the natural lipid comprises an ether link between a lipid tail and a lipid headgroup. In some embodiments, the pharmaceutical composition is admixed with at least one of a pharmaceutically acceptable carrier, diluent, excipient, or adjuvant. In some embodiments, the pharmaceutical composition is topically administrable. In some embodiments, the pharmaceutical composition is parenterally administrable. In some embodiments, the pharmaceutical composition is intravenously administrable.

In some embodiments, the present invention provides a composition comprising a physiologically effective amount of TTA or a derivative thereof, the composition characterized in by a substantial lack of side effects when administered to a human subject, the side effects selected from the group consisting of lethargy, muscle cramps, and muscle pain. In some embodiments, the physiologically effective amount is from about 10 mg to 5 g TTA. In some embodiments, the physiologically effective amount is from about 100 mg to 3 g TTA. In some embodiments, the substantial lack of side effects is characterized by the presence of the side effects in less than 5% of a population. In some embodiments, the substantial lack of side effects is characterized by the presence of the side effects in less than 1% of a population. In some embodiments, the composition comprises at least one fatty acid in addition to the TTA or a derivative thereof. In some embodiments, the derivative of TTA is an ester, triglyceride, or phospholipid comprising a TTA moiety. In some embodiments, the composition is produced by distilling 1-bromotetradecane to remove contaminants and provide distilled 1-bromotetradecane, and reacting the distilled 1-bromotetradecane with a chemical moiety to provide TTA.

In some embodiments, the lipid compositions described above (e.g., the natural lipid compositions and structured lipid compositions) may be used in combination with one or more sialic acid analogs. As used herein sialic acid analogs include sialic acids and sialic acid precursors. Preferably, sialic acids or sialic acid precursors are selected from the group consisting of n-glycolylneuraminic acid, n-acetylneuraminic acid and N-Acetyl-D-mannosamine. In some embodiments, the composition may comprise two or more of the following sialic acids: Neuraminic acid, 5-N-Acetyl-4-O-acetyl-neuraminic acid, 5-N-Acetyl-7-O-acetyl-neuraminic acid, 5-N-Acetyl-8-O-acetyl-neuraminic acid, 5-N-Acetyl-9-O-acetyl-neuraminic acid, 5-N-Acetyl-4,9-di-O-acetyl-neuraminic acid, 5-N-Acetyl-7,9-di-O-acetyl-neuraminic acid, 5-N-Acetyl-8,9-di-O-acetyl-neuraminic acid, 5-N-Acetyl-7,8,9-tri-O-acetyl-neuraminic acid, 5-N-Acetyl-9-O-L-lactyl-acetyl-neuraminic acid, 5-N-Acetyl-4-O-acetyl-9-O-lactyl-acetyl-neuraminic acid, 5-N-Acetyl-8-O-methyl-neuraminic acid, 5-N-Acetyl-9-O-acetyl-8-O-methyl-neuraminic acid, 5-N-Acetyl-8-O-sulpho-neuraminic acid, 5-N-Acetyl-9-O-phosphoro-neuraminic acid, 5-N-Acetyl-2-deoxy-2,3-didehydro-neuraminic acid, 5-N-Acetyl-9-O-acetyl-2-deoxy-2,3-didehydro-neuraminic acid, 5-N-Acetyl-2-deoxy-2,3-didehydro-9-O-lactyl-neuraminic acid, 5-N-Acetyl-2,7-anhydro-neuraminic acid, 4-O-Acetyl-5-N-glycolyl-neuraminic acid, 7-O-Acetyl-5-N-glycolyl-neuraminic acid, 8-O-Acetyl-5-N-glycolyl-neuraminic acid, 9-O-Acetyl-5-N-glycolyl-neuraminic acid, 7,9-Di-O-acetyl-5-N-glycolyl-neuraminic acid, 8,9-Di-O-acetyl-5-N-glycolyl-neuraminic acid, 7,8,9-Tri-O-acetyl-5-N-glycolyl-neuraminic acid, 5-N-glycolyl-9-O-lactyl-neuraminic acid, 5-N-glycolyl-8-O-methyl-neuraminic acid, 9-O-Acetyl-5-N-glycolyl-8-O-methyl-neuraminic acid, 7,9-di-O-Acetyl-5-N-glycolyl-8-O-methyl-neuraminic acid, 5-N-glycolyl-8-O-sulpho-neuraminic acid, N-(O-acetyl)glycolylneuraminic acid, N-(O-Methyl)glycolylneuraminic acid, 2-Deoxy-2,3-didehydro-5-N-glycolyl-neuraminic acid, 9-O-Acetyl-2-deoxy-2,3-didehydo-5-N-glycolyl-neuraminic acid, 2-Deoxy-2,3-didehydro-5-N-glycolyl-9-O-lactyl-neuraminic acid, 2-Deoxy-2,3-didehydro-5-N-glycolyl-8-O-methyl-neuraminic acid, 2,7-Anhydro-5-N-glycolyl-neuraminic acid, 2,7-Anhydro-5-N-glycolyl-8-O-methyl-neuraminic acid, 2-Keto-3-deoxynononic acid, and 9-O-Acetyl-2-keto-3-deoxynononic acid. In some embodiments, the compositions may comprise 2, 3, 4, 5, 6, 7, 8, 9, 10 or more sialic acid analogs. In some embodiments, the sialic acid analogs have a purity selected from the group consisting of greater than 90%, 95%, 99%, and 99.5% pure.

The sialic acid precursor may be co-formulated in the same delivery vehicle as the lipid composition, or may be provided in a separated delivery vehicle. In some embodiments, the sialic acid composition or sialic acid precursor composition is provided in a daily dosage selected from the group consisting of 1 microgram to 100 mg/day, 100 microgram to 20 mg/day, and 200 microgram to 10 mg/day. In some embodiments, the sialic acid composition or sialic acid precursor composition is provided in a daily dosage selected from the group consisting of 0.1 to 10 mg/150 kg subject/day, 0.3 to 5 mg/150 kg subject/day, and 0.5 to 2 mg/150 kg subject/day. In some embodiments, the administering is selected from the group consisting of enteral administration, parenteral administration, oral administration, sublingual administration, subcutaneous administration, intramuscular administration, and intravenous administration.

Additional embodiments will be apparent to persons skilled in the relevant art based on the teachings contained herein.

DETAILED DESCRIPTION

Provided herein is technology relating to natural lipids containing non-β-oxidizable fatty acids and particularly, but not exclusively, to compositions and methods related to the production and therapeutic use of natural lipids containing non-β-oxidizable fatty acids. This technology is described below, wherein the section headings are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, "feeding" refers to providing a substance, compound, composition, etc. to a living organism. For example, the substance, compound, composition, etc. may be an energy source, a carbon source, a nutrient, or a source of other elements, molecules, and/or precursors of biological molecules that are used by the living organism and/or are metabolized (e.g., catabolized, anabolized) by the living organism. The substance, compound, composition, etc. is not necessarily a substance, compound, composition, etc. that the living organism encounters in its native milieu, but may be a synthetic substance, compound, composition, etc. or a natural substance, compound, composition, etc. that is nevertheless used by the living organism for metabolism. The substance, compound, composition, etc. may be added to a culture medium or a substrate in which or on which the living organism lives and/or grows.

As used herein, "active" or "activity" refers to native or naturally occurring biological and/or immunological activity.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the terms "subject" and "patient" refer to any animal, such as a mammal like a dog, cat, bird, livestock, and preferably a human (e.g., a human with a disease such as obesity, diabetes, or insulin resistance).

As used herein, the term "individual" refers to vertebrates, particularly members of the mammalian species. The term includes but is not limited to domestic animals, sports animals, primates, and humans.

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present technology.

As used herein, the terms "alkyl" and the prefix "alk-" are inclusive of both straight chain and branched chain saturated or unsaturated groups, and of cyclic groups, e.g., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms. Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulfhydryl, alkylthio, arylthio, halogen, alkylsilyl, hydroxyl, fluoroalkyl, perfluoroalkyl, amino, aminoalkyl, disubstituted amino, quaternary amino, hydroxyalkyl, carboxyalkyl, and carboxyl groups. When the prefix "alk" is used, the number of carbons contained in the alkyl chain is given by the range that directly precedes this term, with the number of carbons contained in the remainder of the group that includes this prefix defined elsewhere herein. For example, the term "$C_1$-$C_4$ alkaryl" exemplifies an aryl group of from 6 to 18 carbons (e.g., see below) attached to an alkyl group of from 1 to 4 carbons.

As used herein, the term "aryl" refers to a carbocyclic aromatic ring or ring system. Unless otherwise specified, aryl groups are from 6 to 18 carbons. Examples of aryl groups include phenyl, naphthyl, biphenyl, fluorenyl, and indenyl groups.

As used herein, the term "heteroaryl" refers to an aromatic ring or ring system that contains at least one ring heteroatom (e.g., O, S, Se, N, or P). Unless otherwise specified, heteroaryl groups are from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl groups.

As used herein, the term "heterocycle" refers to a non-aromatic ring or ring system that contains at least one ring heteroatom (e.g., O, S, Se, N, or P). Unless otherwise specified, heterocyclic groups are from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents selected from the group consisting of $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, alkaryl (where the alkyl group has from 1 to 4 carbon atoms), and alkheteroaryl (where the alkyl group has from 1 to 4 carbon atoms).

As used herein, the term "alkoxy" refers to a chemical substituent of the formula —OR, where R is an alkyl group. By "aryloxy" is meant a chemical substituent of the formula —OR', where R' is an aryl group.

As used herein, the term "$C_{x-y}$ alkaryl" refers to a chemical substituent of formula —RR', where R is an alkyl group of x to y carbons and R' is an aryl group as defined elsewhere herein.

As used herein, the term "$C_{x-y}$ alkheteraryl" refers to a chemical substituent of formula RR", where R is an alkyl group of x to y carbons and R" is a heteroaryl group as defined elsewhere herein.

As used herein, the term "halide" or "halogen" or "halo" refers to bromine, chlorine, iodine, or fluorine.

As used herein, the term "non-vicinal O, S, or N" refers to an oxygen, sulfur, or nitrogen heteroatom substituent in a linkage, where the heteroatom substituent does not form a bond to a saturated carbon that is bonded to another heteroatom.

For structural representations where the chirality of a carbon has been left unspecified it is to be presumed by one skilled in the art that either chiral form of that stereocenter is possible.

Embodiments of the Technology

The compounds according to the technology are analogues of naturally occurring compounds and as such are recognized by the same systems that process the natural compounds, including the enzymes that β- and in some cases ω-oxidize natural long chain fatty acids. The analogues differ from their naturally occurring counterparts in that they cannot be completely oxidized in this manner Non-β-Oxidizable Analogues The compounds according to the technology comprise non-β-oxidizable fa acid analogues as represented by the formula

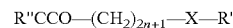
R"CCO—$(CH_2)_{2n+1}$—X—R' wherein X is a sulfur atom, a selenium atom, an oxygen atom, a $CH_2$ group, a SO group, or a $SO_2$ group; n is an integer of 0 to 11; R' is a linear or branched alkyl group, saturated or unsaturated, optionally substituted, wherein the main chain of the R' contains from 13 to 23 carbon atoms and optionally one or more heterogroups selected from the group comprising an oxygen atom, a sulfur atom, a selenium atom, an oxygen atom, a $CH_2$ group, a SO group, and a $SO_2$ group; and R" is a hydrogen atom or an alkyl group containing from 1 to 4 carbon atoms.

Embodiments of the technology relate to phospholipids comprising a non-β-oxidizable fatty acid analogues. That is, in some embodiments the compounds are structures derived from one or more of said non-β-oxidizable fatty acid analogues, as represented by the general formulae I or II

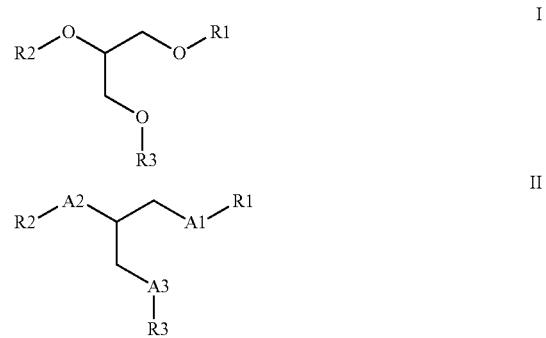

wherein in I, R1, R2, and R3 represent:
i) a hydrogen atom;
ii) a group having the formula CO—R or R in which R is a linear or branched alkyl group, saturated or unsaturated, optionally substituted; and the main chain of R contains from 1 to 25 carbon atoms;
iii) a group having the formula CO—$(CH_2)_{2n+1}$—X—R' or $(CH_2)_{2n+1}$—X—R', wherein X is a sulfur atom, a selenium atom, an oxygen atom, a $CH_2$ group, a SO group, or a $SO_2$ group; n is an integer from 0 to 11; and R' is a linear or branched alkyl group, saturated or unsaturated, optionally substituted; and the main chain of R' contains from 13 to 23 carbon atoms and optionally one or more heterogroups selected from an oxygen atom, a sulfur atom, a selenium atom, an oxygen atom, a $CH_2$ group, a SO group, and a $SO_2$ group; or iv) an entity that is a $PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol), or $PO_3(CHOH)_6$ (inositol), wherein R1, R2, and R3 are chosen independently from i), ii), iii), or iv), but at least one of R1, R2, or R3 is defined by iii); and/or, wherein in II, A1, A2 and A3 are chosen independently and represent an oxygen atom, a sulfur atom, or an N—R4 group in which R4 is a hydrogen atom or a linear or branched alkyl group, saturated or unsaturated, optionally substituted, and contains from 1 to 5 carbon atoms; and R1, R2, and R3 represent i) a hydrogen atom or a linear or branched alkyl group, saturated or unsaturated, optionally substituted, containing from 1 to 23 carbon atoms; or ii) a group having the formula CO—R in which R is a linear or branched alkyl group, saturated or unsaturated, optionally substituted; and the main chain of said R contains from 1 to 25 carbon atoms;

iii) a group having the formula CO—$(CH_2)_{2n+1}$—X—R', wherein X is a sulfur atom, a selenium atom, an oxygen atom, a $CH_2$ group, a SO group, or a $SO_2$ group; n is an integer from 0 to 11; and R' is a linear or branched alkyl group, saturated or unsaturated, optionally substituted, wherein the main chain of R' contains from 13 to 23 carbon atoms and optionally one or more heterogroups that is an oxygen atom, a sulfur atom, a selenium atom, an oxygen atom, a $CH_2$ group, a SO group, or a $SO_2$ group; or iv) an entity that is a $PO_3CH_2CHNH_3COOH$ (serine), $PO_3CH_2CH_2NH_3$ (ethanolamine), $PO_3CH_2CH_2N(CH_3)_3$ (choline), $PO_3CH_2CHOHCH_2OH$ (glycerol), or $PO_3(CHOH)_6$ (inositol), wherein R1, R2, and R3 are chosen independently from i), ii), iii), or iv), but at least one of R1, R2, or R3 is defined by iii).

These compounds are analogues of naturally occurring monoacylglycerols, diacylglycerols, or triacylglycerols; or phospholipids including phosphatidyl serine, phosphatidyl choline, phosphatidyl ethanolamine, phosphatidyl inositol, phosphatidyl glycerol, and diphosphatidyl glycerol. Said compounds may also comprise a substitution in the glycerol backbone, as shown in formula II. Said substitution of the oxygen(s) is achieved by replacing the oxygen(s) with sulfur or a nitrogen containing group. This may block hydrolysis before uptake by the intestines, thus increasing the bioavailability of the compounds.

These structures derived from one or more non-β-oxidizable fatty acid entities have their effect because the fatty acid analogues are not capable of being fully β-oxidized. The structures may have an effect as complete structures and/or as naturally resulting degradation products comprising the fatty acid analogues. Because the compounds are not fully β-oxidized, they will build up and trigger an increase in the β-oxidation of naturally occurring fatty acids. Many of the effects of the compounds according to the technology relate to this increase in β-oxidation.

During β-oxidation, a fatty acid is enzymatically cleaved between carbons 2 and 3 (relative to the carboxylic end of the fatty acid), resulting in the removal of two carbon atoms as acetic acid. This step is then repeated on the resulting shorter fatty acid and repeated again until the fatty acid is fully oxidized. β-oxidation is the usual way in which the majority of fatty acids is catabolized in vivo. The compounds according to the technology block β-oxidation due to the presence of a non-oxidizable group (e.g., S, O, SO, $SO_2$, $CH_2$ or Se) in the X position in the structural formula of the present technology. These compounds all block β-oxidation in the same manner Furthermore, the compounds may contain more than one block. For example, the R' comprising X may also optionally comprise one or more additional heterogroups selected from the group comprising an oxygen atom, a sulfur atom, a selenium atom, an oxygen atom, a $CH_2$ group, a SO group, and a $SO_2$ group. As an example, one may insert two or three sulfurs as X to induce a change in the degradation of the fatty acid and thus provide a modulated effect Multiple sulfur atoms would also modulate the polarity and stability. From a pharmacological viewpoint, it is generally desirable to present a spectrum of compounds rather than just one single compound to avoid or counteract problems with resistance.

Embodiments of the technology define not only the identity of X, but also the position of X. The distance of X from the carboxylic end of the fatty acid is defined by how many $CH_2$ groups are positioned between X and the carboxylic end of the fatty acid, which is defined by $(CH_2)_{2n+1}$, where n is an integer from 0 to 11. Thus, there is an odd number of $CH_2$ groups; that is, the position of X relative to the carboxyl group is such that X blocks β-oxidation. The range of n is chosen to include all variations of the fatty acid analogue that have the desired biological effect. Since β-oxidation in theory can work on infinitely long molecules, n could be infinite, but in practice this is not so. The fatty acids that normally undergo β-oxidation are usually 14 to 24 carbon atoms long, and this length is therefore most ideal for undergoing enzymatic β-oxidation. The ranges of n and R' are thus given so that the fatty acid analogues cover this range. Likewise, option ii of formulae I and II defines R to have from 1 to 25 carbon groups, and option i of formula II defines the alkyl group to contain from 1 to 23 carbon atoms to be analogous to naturally occurring compounds. The total number of carbon atoms in the fatty acid backbone is approximately between 8 and 30, e.g., in some embodiments between 12 and 26. This size range is also desirable for the uptake and transport through cell membranes of the fatty acid analogues described.

Although β-oxidation is blocked by fatty acid analogues wherein the β-oxidation blocker X is an odd number of positions from the carboxylic end block, the biological effect varies as a function of the position of X due to the difference in biological degradation time of the various compounds. Experiments show the effect of moving X further from the carboxylic fatty acid end. In particular, these experiments show that mitochondrial β-oxidation of fatty acid analogues in the liver varied as a function of sulfur position, e.g., in the 3, 5 and 7 positions relative to the carboxyl ends. The activities were 0.81 for sulfur in the 3rd position, 0.61 for sulfur in the 5th position, 0.58 for sulfur in the 7th position, and 0.47 for the non β-oxidation blocking control palmitic acid (see, e.g., U.S. Pat. No. 8,178,713). Thus, β-oxidation is indeed blocked to varying degrees depending on the position of the block. The blocking effect lessens as the blocking group is moved further away from the carboxylic end because the β-oxidation takes longer to reach the block and more of the fatty acid analogue is degraded. However, as the relative decline is great for moving the block from the 3rd to 5th position and the relative decline is smaller for moving the block from the 5th to the 7th position, it is reasonable to assume that the relative decline between positions will continue to lessen as the block is placed further down the chain. It is thus expected that no effect (compared to the control) will be seen at very far distances from the carboxyl end.

Accordingly, the technology encompasses fatty acid analogues and other compounds represented by the general formulas I and II comprising fatty acid analogues that block β-oxidation. In some embodiments, different compounds have a block at different distances from the carboxylic end of the analogues to modulate the effect on β-oxidation. In some embodiments, the modulation differs under varying conditions, in different tissues, with varying dosages, and by changing the fatty acid analogue, e.g., to one that is resistant to metabolisis. Thus, the technology includes all embodiments of the compositions in which the distance of the β-oxidation blocker from the carboxylic end provides a fatty acid analogue that is biologically relevant.

Although fatty acid analogues as described with a block in the X position cannot undergo β-oxidation, they may still undergo ω-oxidation. This is a much less common and slower biological process that oxidizes the fatty acid from the methyl/hydrophobic head group, here termed R'. In this pathway, the carbon atom at the ω-end of the fatty acid is hydroxylated by a member of the cytochrome P450 enzyme family. This hydroxylated fatty acid is then converted into an aldehyde by an alcohol dehydrogenase, and subsequently this aldehyde is converted into a carboxyl group by an aldehyde dehydrogenase. As a consequence, the final product of the pathway is a dicarboxylic fatty acid, which can be degraded further by ω-oxidation from the ω-end.

ω-oxidation is believed to be the main pathway for degradation of the fatty acid analogues as described with a block in the X position. Fatty acid analogues in which R' was changed by introducing a triple bond at the methyl end of the fatty acid analogue block ω-oxidation. In particular, this modification resulted in the fatty acid analogue 3-thia-15-heptadecyne, which when tested showed a substantially increased degradation time in vivo. Thus, this modification finds use in embodiments of the technology to potentiate the effects of the β-oxidizable fa acid analogues by further slowing down their breakdown.

Based upon knowledge of how ω-oxidation occurs, a double bond will also block ω-oxidation. Thus, fatty acid analogues comprising a double bond are also included in the definition of the methyl/hydrophobic head group end of the molecule, here termed R'. That is, it may be saturated or unsaturated. A branch may also block oxidation, so R' is also defined as linear or branched.

To block ω-oxidation by the insertion of a substitute in R', the R' may be substituted in one or several positions with heterogroups such as an oxygen atom, a sulfur atom, a selenium atom, an oxygen atom, a $CH_2$ group, a SO group, or a $SO_2$ group. R' may also be substituted with one or more compounds of a fluoride, chloride, hydroxy, $C_1$-$C_4$ alkoxy, $C_1$-$C_4$ alkylthio, $C_2$-$C_5$ acyloxy, or $C_1$-$C_4$ alkyl.

Thus, the compounds according to the present technology are either fatty acids analogous to naturally occurring fatty acids, which are not capable of being β-oxidized, or naturally occurring lipids comprising said fatty acid analogues. In vivo, the fatty acid analogues show a strong preference for being incorporated into phospholipids. Incorporating fatty acid analogues in naturally occurring lipids (e.g., monoglycerides, diglycerides, triglycerides, and/or phospholipids) produces a compound with different absorption characteristics compared to the fatty acids. In addition, it is contemplated that incorporating fatty acid analogues in naturally occurring lipids (e.g., monoglycerides, diglycerides, triglycerides, and/or phospholipids) may also increase the bioavailability or stability.

For example, some embodiments of the technology relate to a triacylglycerol that includes a fatty acid that is not capable of being β-oxidized. Such compounds are encompassed by formulas I and II. If such a triacylglycerol were taken orally, for instance in an animal food product, it would probably be transported like any triacylglycerol, e.g., from the small intestine in chylomicrons to the liver; then to the blood in lipoproteins to be stored in the adipose tissue or used by muscles, heart, or the liver; then by hydrolysis of the triacylglycerol into glycerol and three free fatty acids. The free fatty acids would at this point be the fatty acid analogue parent compound.

Embodiments also encompass glycerophospholipid derivatives of the fatty acid analogues that block β-oxidation, including, but not limited to, phosphatidylcholines, phosphatidylethanolamines, phosphatidylinositols, phosphatidylserines, and phosphatidylglycerols.

In some embodiments, the fatty acid analogues that block β-oxidation are incorporated into a sphingolipid derivative such as ceramide or a sphingomyelin. Like glycerophospholipids complexes, these compounds would be water insoluble and hydrophobic, and thus pass through biological membranes.

Additional embodiments include polar complexes such as, but not limited to, lysophospholipids, phosphatidic acids, alkoxy compounds, glycerocarbohydrates, gangliosides, and cerebrosides.

In some embodiments, a non-β-oxidizable fatty acid analogue is incorporated into an archaeal phospholipid (e.g., as produced by members of the Archaea). The archaeal lipids are analogous to glycerolipids from Bacteria and Eukaryotes, but have some distinguishing features. For example, archaeal lipids generally comprise a core lipid (e.g., archaeol or caldarchaeol) and polar head groups or glycosides that are linked to one of the core lipids. In addition, the hydrocarbon chains (e.g., a non-β-oxidizable fatty acid analogue) are bound at the sn-2 and sn-3 positions of the glycerol moiety and thus the glycerophosphate backbone of archaeal phospholipids is sn-glycerol-1-phosphate. The hydrocarbon chains are bound to the glycerol by ether linkages. In some of these lipids, the hydrophobic tails are methyl-branched isoprenoids, e.g., derived from (all-E) geranylgeranyl diphosphate (GGPP). Archaeal lipids comprise polar phospholipid head groups such as ethanolamine, L-serine, glycerol, myo-inositol, choline, dimethylaminopentanetetrol, trimethylaminopentanetetrol, glucosaminyl-myo-inositol, and glucosyl-myo-inositol. See, e.g., Koga and Morii (2005), "Recent Advances in Structural Research on Ether Lipids from Archaea Including Comparative and Physiological Aspects", *Biosci Biotechnol Biochem* 69: 2019-34; Koga and Morii (2007), "Biosynthesis of Ether-Type Polar Lipids in Archaea and Evolutionary Considerations", *Microbiol Mol Biol Rev*, 71: 97. Archaeal lipid biosynthetic pathways are well characterized. Indeed, portions of archaeal lipid biosynthetic pathways (e.g., genes encoding archaeal G-1-P dehydrogenase, GGPP synthase, GGGP synthase, and DGGGP synthase) have been reconstituted in *Escherichia coli*, thus providing a manipulable and tractable system for the production and isolation of archaeal lipids in a bacterium. See, e.g., Yokoi, et al. (2012), "Archaeal Phospholipid Biosynthetic Pathway Reconstructed in *Escherichia coli*", *Archaea* 2012.

Although there can be large structural differences between different compounds comprising non β-oxidizable fatty acid entities according to the technology, the biological functions of all the compounds are expected to be very similar because they all block β-oxidation in the same manner.

This inability of the fatty acid analogues to be β-oxidized (and in some embodiments, ω-oxidized) causes the analogues to build up in the mitochondria, which triggers the β-oxidation of the in vivo naturally occurring fatty acids. This in turn leads to the biological effects associated with the compounds provided herein according to the present technology. See, e.g., Berge R K et al. (2002) Curr Opin Lipidol 13 (3):295-304.

Tetradecylthioacetic Acid (TTA)

The technology relates to phospholipids, phospholipid derivatives, triacylglycerides (TAGs), and non-natural lipids, e.g., for use in therapeutic applications. In particular, these lipids and phospholipids incorporate the known sulfur fatty acid, tetradecylthioacetic acid (TTA) as well as its unsaturated analogues, dTTA and tTTA. Tetradecylthioacetic acid (TTA) is a fatty acid analogue of the technology according to formula I having a structure, in some embodiments, as shown below.

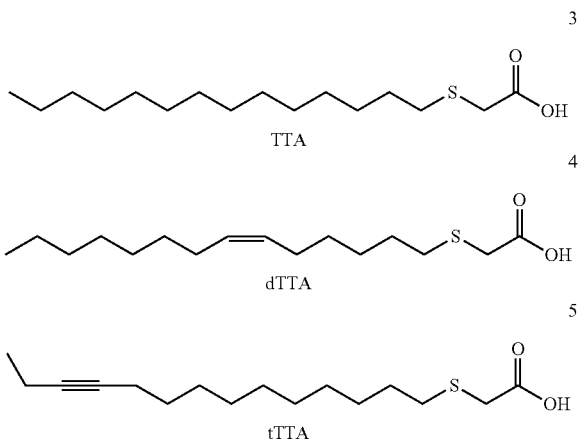

It is understood that analogues that contain one of Se, SO, $SO_2$, O, or $CH_2$ in place of sulfur also provide useful pharmaceutical activity. In addition, the length and degrees of saturation of the alkyl chains can also be varied.

The sulfur atom is more electronegative than carbon. Hence, the 3-thia acid is slightly more acidic than its corresponding fatty acid. Thia fatty acids are also more polar and slightly more soluble in water than fatty acids of corresponding chain length.

Biological Effects of Tetradecylthioacetic Acid (TTA)

TTA is a modified fatty acid that has a number of powerful effects demonstrable both in vivo and in vitro on living organisms (see, e.g., Int'l Pat. App. Nos WO01/68582 (PCT/NO01/00082), WO99/58121 (PCT/N099/00135), WO99/58122 (PCT/NO99/00136), and WO99/58123 (PCT/N099/00149); Berg, R. K. and Hvattuu, E. (1994), Pharmac Ther 61: 345; Skrede, S. et al (1997), Biochim Biophys Acta 1344: 115). While TTA has properties very similar to natural fatty acids, it cannot be oxidized by mitochondrial β-oxidation. Importantly, though, TTA significantly increases the oxidation of other fatty acids. Finally, despite the fact that TTA is not catabolized by β-oxidation, it is metabolized in most ways as a normal saturated fatty acid. For example, it is incorporated into phospholipids.

TTA affects antioxidant status at different levels, e.g., by changing the antioxidant defense system in addition to being an antioxidant itself through its free radical scavenging capacity. Addition of TTA may prevent the oxidative modification of LDL particles in plasma and reduce the generation of lipid peroxides.

The fatty acid β-oxidation pathway is the main pathway for the metabolism of fats. The initial and rate limiting reaction is carried out in the peroxisomes of the liver by acyl-CoA oxidase. Acyl-CoA oxidase catalyzes the dehydrogenation of acyl-CoA thioesters to the corresponding trans-2-enoyl CoA.

Compositions comprising TTA and particular plant and animal oils have biological effects on acyl-CoA oxidase. For example, TTA alone effects a large increase in acyl-CoA oxidase activity. When combined with fish and/or olive oil, the composition showed a slight potentiation of the increased acyl-CoA oxidase activity effected by TTA. In contrast, sunflower oil does not increase the activity of TTA when the sunflower oil and TTA were administered together. Soy oil without TTA had negligible effects on acyl-CoA oxidase activity, but combined with TTA it exhibited a 60% increase when compared to the effects of TTA alone. See, e.g., U.S. Pat. Appl. Pub. No. 2007009608.

In addition, non-β-oxidizable fatty acid entities such as TTA modulate biological phospholipid levels, both alone and in compositions comprising various plant oil and/or fish oils. For example, sunflower and/or fish oil in combination with TTA reduce phospholipid levels more than either TTA or the oils alone. While soy oil and olive oil alone cause an increase in phospholipid levels, these oils substantially potentiated the ability of TTA to decrease phospholipid levels. In particular, soy oil alone increased phospholipid levels by 10%, but a composition comprising both TTA and soy oil lowered phospholipid levels by an additional 40% compared to TTA alone. See, e.g., U.S. Pat. Appl. Pub. No. 2007009608.

Furthermore, non β-oxidizable fatty acid entities such as TTA modulate biological cholesterol levels, both alone and in compositions comprising various plant oil and/or fish oils. For example, TTA lowered cholesterol levels more than any plant or fish oil alone; compositions comprising both TTA and sunflower oil and/or fish oil lowers cholesterol levels more than TTA or either oil alone. While olive and soy oil alone increase cholesterol levels, these oils substantially potentiated the ability of TTA to decrease cholesterol levels. This TTA potentiating effect was greatest with compositions comprising TTA and soy oil, which reduced the cholesterol level by 60% when compared with TTA alone.

TTA reduces plasma triacylglycerol level by increasing the number of mitochondria and stimulating mitochondrial β-oxidation of normal saturated and unsaturated fatty acids to ketone bodies (Froyland L et al. (1997), J Lipid Res 38: 1851-1858). This effect is potentiated by the addition of plant and fish oils to compositions comprising TTA. Olive, sunflower, and fish oil alone all lower triacylglycerol levels. While sunflower and fish oils lower triacylglycerol levels more than TTA alone, these oils further potentiate the effect of TTA beyond that seen for either the oils or TTA alone. Furthermore, while soy oil increases triacylglycerol levels by 15%, compositions comprising both TTA and soy oil lower triacylglycerol levels more than TTA or soy oil alone, e.g., by a factor of 130%.

According to embodiments of the technology, the fatty acid derivatives have one or more therapeutic effects. For example, the fatty acid derivatives fund use in the treatment of hyperlipidemia conditions and in reducing the concentration of cholesterol and triglycerides in the blood of mammals. In addition, selenium analogues have the same properties as well as inhibiting the oxidative modification LDL (see, e.g., EP0345038; WO97/03663 (PCT/N095/00195)). 2). The fatty acid analogues also find use for the treatment of and/or prevention of obesity, hypertension, fatty liver, and multi-metabolic syndrome ("Syndrome X"). (see, e.g., WO99/58121 (PCT/N099/00135)); for the treatment and/or the prevention of diabetes (Type I and II), hyperglycaemia, hyperinsulinemia, and reduced sensitivity to insulin (see, e.g., WO99/58122 (PCT/NO99/00136)); for the treatment and/or prevention of primary stenosis, secondary stenosis, and a disease caused by procedural vascular trauma and pathological proliferation of smooth muscle cells, and increase level of plasma homocystein (see, e.g., WO99/58123 (PCT/N099/00149)); for the treatment and/or prevention of cancer (e.g., treatment and/or prevention of primary and secondary neoplasms (see, e.g., WO02/03983 (PCT/NO01/00301)), for the treatment and/or prevention of proliferative skin disorders (see, e.g., WO 02/26218), and for the treatment and/or prevention of inflammatory disorders (see, e.g., WO 02/43728).

Accordingly, the fatty acid lipid derivatives of the present technology have corresponding therapeutic effects and/or biological properties.

TTA Modulation of PPAR

In particular, the fatty acid derivatives modulate the activity of members of the peroxisome proliferator-activated receptor (PPAR) family. The PPAR are pleiotropic regulators of cellular functions such as cellular proliferation, differentiation, and lipid homeostasis (Ye, et al. (2001) *Diabetes* 50: 411-417). The PPAR family is comprised of three subtypes; PPARα, PPARβ, and PPARγ. Forms of TTA are potent ligands of PPARα. (Forman, et al. (1997) *Proc Natl Acad Sci* 94:4312-4317; Gottlicher, et al. (1993) *Biochem Pharmacol* 46: 2177-2184; Berge, et al. (1999) *Biochem J* 343: 191-197) and activate PPARβ and PPARγ as well (Raspe, et al. (1999) *J Lipid Res* 40: 2099-2110). As a PPARα activator, TTA stimulate the catabolism of fatty acids by increasing their cellular uptake. Lowering the plasma triglyceride levels with TTA caused a shift in liver cellular metabolism towards PPARα-regulated fatty acid catabolism in mitochondria (Graf, et al. (2003) *J Biol Chem* 278: 30525-33). The effect of TTA on plasma triacylglycerol is direct by PPARα activation, which is demonstrated by the abolishment of this effect in PPARα knockout mice.

PPAR ligands affect proliferation of various cancer cell lines. TTA in particular has been found to reduce proliferation of many cancer cell lines (Berge, et al. (2001) *Carcinogenesis* 22:1747-1755; Abdi-Dezfuli, et al. (1997) *Breast Cancer Res Treat* 45: 229-239; Tronstad, et al. (2001) *Biochem Pharmacol* 61: 639-649; Tronstad, et al. (2001) *Lipids* 36: 305-313). This reduction is related to reduction in triacylglycerol levels (Tronstad, et al. (2001) *Biochem Pharmacol* 61: 639-649) and is mediated by both PPAR dependent and independent pathways (Berge, et al. (2001) *Carcinogenesis* 22: 1747-1755). It has also been shown that fermented soy protein improves TTA's ability to lower triacylglycerol levels; it is therefore contemplated that fermented soy protein also improves the anti-proliferative effects of TTA, thus improving TTA's cancer prevention and treatment abilities. For example, TTA may be used for the prevention and/or treatment of cancer including inhibition of: primary and secondary neoplasms, the growth of tumors, invasion of a primary tumor into connective tissue, and formation of secondary tumors (see, e.g., NO 2002 5930).

In general, PPAR agonists modulate the inflammatory response. TTA modulate inflammatory responses by depressing the release of inflammatory cytokine interleukin-2 and suppressing PHA stimulated proliferation of peripheral mononuclear cells (Aukrust, et al. (2003) *Eur J Clin Invest* 33: 426-33). The modulation of cytokines by TTA may be mediated by PPAR, through altering prostaglandin levels, or by modification of lipid mediated signal transduction, the latter which also is the proposed mechanism of action for polyunsaturated fatty acids, e.ge, as found in some oils.

According to embodiments of the technology, protein material, and optionally oil, in combination with non β-oxidizable fatty acid entities potentiates the effect of fatty acid entities on inflammatory disorders, including immune mediated disorders such as rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegener's granulomatosis), inflammatory bowel diseases, Crohn's disease, non-specific colitis, pancreatitis, nephritis, cholestatis/fibrosis of the liver, and acute and chronic allograft rejection after organ transplantation, as well as proliferate skin disorders like psoriasis, atopic dermatitis, non-specific dermatitis, primary irritant contact-dermatitis, allergic contact-dermatitis, lamellar ichthyosis, epidermolytic hyperkeratosis, pre-malignant sun-induced keratosis, and seborrhea, and diseases that have an inflammatory component such as, e.g., Alzheimer's disease or impaired/improvable cognitive function. See e.g., U.S. Pat. No. 7,659,242.

Substances such as oils, e.g., fish oils, and proteins, e.g., fermented soy protein, potentiate the modulatory effects of TTA on lipid metabolism. That is, compositions comprising TTA and an oil such as a fish oil and/or a protein such as a fermented soy protein material have a synergistic effect on lipid metabolism, e.g., the effect is more than the additive effects of TTA and an oil (e.g., a fish oil) and/or a protein product (e.g., a fermented soy product) alone. See, e.g., U.S. Pat. No. 7,659,242.

Synthesis of TTA and TTA Compounds

Synthetic routes to TTA and molecules comprising TTA are provided in, e.g., U.S. Pat. Nos. 5,093,365; 6,046,237; 6,365,628; 6,417,232; 6,441,036; 7,026,356; 7,378,443; 7,902,399; 8,088,825; preparation of mono-, di-, and triglycerides and nitrogen comprising lipids according to the technology are disclosed in detail in U.S. Pat. No. 7,375,135; and the synthesis of phospholipids comprising TTA are provided in, e.g., U.S. Pat. No. 8,178,713.

Some compositions of TTA produced for human consumption have been associated with side effects, including lethargy, muscle cramps, and muscle pain. It is likely that these side effects are due to contaminants in some commercially produced TTA products. Accordingly, provided herein are TTA preparations that eliminate or minimize side effects such as lethargy, muscle cramps, and muscle pain. One such improved synthesis is provided in the Examples. In some embodiments, the TTA is used directly to provide a composition according to certain aspects of the technology and in some embodiments the TTA is incorporated into a phospholipid by a living organism.

Isolation of Phospholipids from a Living Organism, Consortium, or System

In some embodiments, the technology relates to isolating phospholipids (e.g., a natural phospholipid and/or an oil) comprising a non-beta-oxidizable fatty acid analogue (e.g., TTA) from one or more living organisms such as a bacterium, alga, archaeon, yeast, etc. Phospholipids make up approximately 10% of the dry weight of a cell. Thus, cultures of cells provide a source for the production and harvesting of phospholipids. Accordingly, in some embodiments, the technology relates to feeding a living organism a non-beta-oxidizable fatty acid analogue (e.g., TTA), which is then incorporated into phospholipid by the living organism, and then isolating the phospholipid, e.g., by biochemical or other isolation and/or purification techniques. In some embodiments, the phospholipid is co-isolated with other biological molecules, substances, entities, etc. that are produced by the living organism. That is, in some embodiments, the technology relates to a composition (e.g., an oil) and/or a method of producing a composition produced from a living organism, wherein the composition comprises a phospholipid (e.g., a natural phospholipid) having a non-beta-oxidizable fatty acid analogue (e.g., TTA) and at least one other biological molecule from the living organism.

The living organism may, in some embodiments, be grown in a controlled culture, e.g., in a defined medium, a semi-defined medium, an undefined medium, a synthetic medium, or a natural medium; under controlled temperature, pressure, volume, and agitation; and in a controlled atmosphere of gases (e.g., a particular mixture of oxygen, carbon dioxide, nitrogen, and other gases, etc.). The culture may comprise a single type of organism (e.g., a single species, sub-species, clone, subtype, isolate, etc.) or the culture may comprise more than one type of organism (e.g., more than one species, sub-species, clone, subtype, isolate, etc.).

In some embodiments, the living organism is a member of the Bacteria; in some embodiments, the living organism is a member of the Eukarya; and, in some embodiments, the living organism is a member of the Archaea, as defined by, e.g., Woese C, Fox G (1977). "Phylogenetic structure of the prokaryotic domain: the primary kingdoms." *Proc Natl Acad Sci USA* 74: 5088-90; Woese C, Kandler O, Wheelis M (1990). "Towards a natural system of organisms: proposal for the domains Archaea, Bacteria, and Eucarya." *Proc Natl Acad Sci USA* 87: 4576-9. In some embodiments, one or more phospholipids according to the technology is or are isolated from a composition of more than one living organism, e.g., a co-culture and/or living system and/or consortium of living organisms that may or may not be categorized in the same phylogenetic kingdom.

It is contemplated that any organism that can be grown in the presence of a non-beta-oxidizable fatty acid analogue such as TTA is encompassed by the present technology. It is contemplated that any organism that can incorporate a non-beta-oxidizable fatty acid analogue such as TTA into a phospholipid is encompassed by the present technology. As discussed elsewhere, it is contemplated that a non-beta-oxidizable fatty acid analogue is metabolized (e.g., anabolized) in the same manner as its natural counterpart save for its resistance to beta-oxidation.

Other Natural Lipids and/or Fatty Acids

While the structure and biological function of many of the major lipids from marine organisms have been studied, less is known of the properties of the structure and function of lipids present in marine organisms in small amounts. Microorganisms such as marine bacteria and algae are the primary source for lipids and/or lipid precursors in marine food chains. Many potentially bioactive compounds are detectable in fish and other marine animals in low amounts, e.g., due to losses in the food chain. These bioactive lipids may be present in a larger amount in microorganisms nearer the base of the food chain That is, it is contemplated that lipid extracts (e.g., oils, fractions, etc.) demonstrate high specific biological activities as isolated from microorganisms.

For example, furan fatty acids have biological activities such as scavenging free radicals (e.g., by reacting readily with peroxyl radicals to generate dioxoenes) and thus may contribute to the protective properties of fish and fish oil diets relative to heart disease. Furan fatty acids are tri- or tetra-substituted furan derivatives comprising either a $C_3$ or $C_5$ side chain in one of the alpha positions and a straight long-chain saturated acid with a carboxylate at its end in the other alpha position.

Furan fatty acids have been found in fish, algae, bacteria, and fungi, and are generated in large amounts by algae and in small to moderate amounts by plants and other microorganisms. Marine organisms (such as fish) and mammals obtain furan fatty acids in food and metabolize them into phospholipids. Furan fatty acids are catabolized to dibasic urofuran acids and excreted in the urine. Due to their molecular structure, furan fatty acids are contemplated to be catabolized more slowly than other lipids in mammals, and thus potentially to be bioactive in relation to energy metabolism.

As discussed elsewhere, unusual lipids (e.g., phytanyl ether lipids) are present in the Archaea, particularly in thermophiles and hyperthermophiles, some of which grow optimally at temperatures higher than 80° C. In addition, unusual lipids have been found in some thermophilic members of the Bacteria. For example, the lipids found in *Thermotoga* spp. (e.g., *T. maritima*) comprise a mixture of ether lipids and ester lipids, mainly polar. Liposomes produced from these lipids demonstrate high stability at high and low temperatures, are resistant to acids and bases, and are resistant to high pressure. In addition, these lipids affect membrane properties and thus may result in altered absorption and permeability of nutrients.

Isolating, Characterizing, and Testing Fatty Acids and/or Lipids from Biological Organisms In some embodiments, the technology relates to isolating and characterizing bioactive fatty acids and/or lipids with specific and unusual molecular structures from living organisms such as marine organisms.

In some embodiments, lipids from one or more organisms (e.g., one or more marine organisms) are isolated, extracted, and/or fractionated, and the products are tested for biological activity, e.g., metabolic effects related to fatty acid and lipid metabolism.

In some embodiments, the testing is performed in relevant animal models or in cell culture. Models will be used to screen for effects related to energy metabolism and mitochondrial functions in addition to modulating membrane properties. In some embodiments, living organisms have been provided (e.g., by feeding) a particular fatty acid, fatty acid analogue, or lipid, e.g., a non-beta-oxidizable fatty acid analogue such as TTA and/or a lipid, lipid extract mixture, isolate, oil, etc. isolated and characterized from a biological organism, system, or consortium.

Based on the results of the characterization and the potential for human applications, selected fractions are further processed in some embodiments for the formulation of nutritional products or products that improve the absorption or bioavailability of bioactive compounds.

In some embodiments, isolation and characterization are performed by analytical chromatography coupled to a flame ionization detector and/or mass spectrometry. For example, see Ivanova, et al. (2009) "Lipidomics: a mass spectrometry based systems level analysis of cellular lipids.", *Curr Opin Chem Biol* 13: 526-31; Albert et al. (2009) "Chromatographic methods for the analyses of 2-halofatty aldehydes and chlorohydrin molecular species of lysophosphatidylcholine." *J Chromatogr B Analyt Technol Biomed Life Sci* 877: 2768-77; Suzuki (2011) "Mass spectrometry-based quantitative analysis and biomarker discovery" Yakugaku Zasshi 131: 1305-9.

For example, embodiments of the technology use lipid extraction and isolation from biological samples. These techniques exploit the high solubility of hydrocarbon chains in organic solvents, for example, chloroform/methanol-based phase partitioning. In some embodiments, the protocols are adapted for complex lipid chemistries and low-abundance and labile lipid metabolites. Lipid separation comprises use of, e.g., thin layer chromatography (TLC), solid-phase extraction (SPE) chromatography (e.g., using a column comprising silica or other stationary phases to separate glycerophospholipids, fatty acids, cholesteryl esters, glycerolipids, and sterols from crude lipid mixtures), and/or high performance liquid chromatography (e.g., normal-phase HPLC or reverse-phase HPLC). For example, normal phase HPLC effectively separates glycerophospholipids on the basis of headgroup polarity, whereas reverse-phase HPLC effectively separates fatty acids such as eicosanoids on the basis of chain length, degree of unsaturation, and substitution. HPLC of lipids may either be performed offline or online where the eluate is integrated with the ionization source of a mass spectrometer. Lipid detection, in some embodiments, comprises use of spectrometric methods, e.g., and soft ionization techniques for mass spectrometry such as electrospray ionization (ESI) and matrix-assisted laser desorption/ionization (MALDI). "Soft" ionization does not cause extensive fragmentation, so that comprehensive detection of an entire range of lipids within a complex mixture can be correlated to experimental conditions or disease state. In addition to ESI and MALDI, the technique of atmospheric pressure chemical ionization (APCI) is used in some embodiments for the analysis of nonpolar lipids.

In some embodiments, lipids are detected using ESI-MS, which depends on the formation of gaseous ions from lipids. It is a soft-ionization method that rarely disrupts the chemical nature of the analyte prior to mass analysis. Various ESI-MS methods have been developed for analysis of different classes, subclasses, and individual lipid species from biological extracts. Comprehensive reviews of the methods and their application have recently been published; see, e.g., Murphy et al. (2001) "Analysis of nonvolatile lipids by mass spectrometry" *Chem Rev* 101: 479-526. The major advantages of ESI-MS are high accuracy, sensitivity, reproducibility, and the applicability of the technique to complex solutions without prior derivatization. Han and coworkers have developed a method known as "shotgun lipidomics", which involves direct infusion of a crude lipid extract into an ESI source optimized for intrasource separation of lipids based on their intrinsic electrical properties. Gross and Han (2007). "Lipidomics in diabetes and the metabolic syndrome" *Meth Enzymol* 433: 73-90. In some embodiments, MALDI is used. MALDI mass spectrometry is a laser-based soft-ionization method often used for analysis of large proteins, but has been used successfully for lipids. The lipid is mixed with a matrix, such as 2,5-dihydroxybenzoic acid, and applied to a sample holder as a small spot. A laser is fired at the spot, and the matrix absorbs the energy, which is then transferred to the analyte, resulting in ionization of the molecule. MALDI-Time-of-flight (MALDI-TOF) MS has become a very promising approach for lipidomics studies, particularly for the imaging of lipids from tissue slides. Schiller al. (2007). "MALDI-TOF MS in lipidomics" *Front Biosci* 12: 2568-79. In some embodiments, APCI is used to detect lipids. The source for APCI is similar to ESI except that ions are formed by the interaction of the heated analyte solvent with a corona discharge needle set at a high electrical potential. Primary ions are formed immediately surrounding the needle, and these interact with the solvent to form secondary ions that ultimately ionize the sample. APCI is particularly useful for the analysis of nonpolar lipids such as triacylglycerols, sterols, and fatty acid esters.

In some embodiments, lipid profiling is used to detect and/or characterize lipids. Lipid profiling is a targeted metabolomics platform that provides a comprehensive analysis of lipid species within a cell or tissue. Profiling based on electrospray ionization tandem mass spectrometry (ESI-MS/MS) is capable of providing quantitative data and is adaptable to high throughput analyses. Klose, et al. (2012). "Flexibility of a Eukaryotic Lipidome—Insights from Yeast Lipidomics" *PLoS ONE* 7: e35063. In some embodiments, lipid profiling techniques are applied to characterize the lipids of an organism such as a plants or a microorganism, e.g., a yeast or alga. A combination of quantitative lipidomic data in conjunction with the corresponding transcriptional data (using gene-array methods) and proteomic data (using tandem MS) enables a systems biology approach to a more in-depth understanding of the metabolic or signaling pathways of interest.

To enrich identified lipids, lipid extracts, fractions, or lipid isolates are fed in some embodiments to a microorganism such as algae in culture. It is contemplated that the algae incorporate rare lipids in phospholipids and other non-neutral lipids, thus enriching the lipids in an esterified form. For these studies, in some embodiments TTA will be used as a model compound to feed to microorganisms.

Characterizing lipids comprises testing lipid extracts, fractions, isolates, oils, etc. for metabolic and other biological effects, e.g., using models such as a mouse model with diet-induced obesity or other transgenic mouse models of metabolic diseases. Diet composition is controlled and monitored as it affects metabolic status as a result of the macronutrients in the food source. Metabolic cages are used to control for gas exchange and food intake. In some testing, transcriptomics and proteomics are used to measure gene expression and protein levels of specific genes.

Mouse models are available (e.g., from Jackson Laboratories) for studying immune responses and metabolism diseases such as those involving lipid metabolism, e.g., problems with cholesterol levels (e.g., hypercholesterolemia, hypocholesterolemia), mitochondrial defects, sensitivity to cold, high blood pressure, insulin resistance, hyperlipidemia, diabetes, cardiovascular disease, steatosis, fasting, hyperglycemia, atherosclerosis, lipogenesis, glucose metabolism, glucose tolerance, oxidative stress, bile acid and lipid homeostasis, leptin, adipose tissue stores, wound healing, obesity, apolipoprotein function, statin treatment for hypercholesterolemia, Alzheimer's disease, fatty liver, effects of diet on skin and coat, appetite, hunger, and satiety, cardiac lipid metabolism, adipocyte physiology, fat metabolism and storage, inflammation, cancer, cholesterol gallstone formation, vitamin E deficiency, muscle lipotoxicity, low density lipoprotein receptor, hepatic clearance of alpha2-macroglobulin and plasma accumulation of remnant lipoproteins, HDL, VLDL, LDL, sitosterolemia, fatty acid and triglyceride biosynthesis, Tangier disease, and life span.

Biological Anabolisis of Lipids

Phospholipids are ubiquitous in nature. In addition to serving as a primary component of cellular membranes and binding sites for intra- and intercellular proteins, some phospholipids in eukaryotic cells, such as phosphatidylinositols and phosphatidic acids are either precursors of or, themselves, membrane-derived second messengers. Most phospholipids contain a diglyceride, a phosphate group, and a simple organic molecule (e.g., choline). The lipid sphingomyelin, however, is derived from sphingosine instead of glycerol. The structure of the phospholipid molecule generally consists of hydrophobic tails (e.g., in some embodiments according to the technology, a hydrophobic tail is a TTA) and a hydrophilic head (e.g., a polar headgroup, e.g., a polar moiety). While, typically, one or both of the hydroxyl groups of the diglyceride are acylated with long-chain fatty acids, alkyl-linked and 1Z-alkenyl-linked (plasmalogen) phospholipids are known, and dialkylether variants are known in the archaea. Phospholipids are subdivided into classes based on the nature of the polar headgroup at the sn-3 position of the glycerol backbone in eukaryotes and eubacteria, or the sn-1 position in the case of archaea. Examples of phospholipids found in biological membranes are phosphatidylcholine (also known as PC, GPCho, or lecithin), phosphatidylethanolamine (PE or GPEtn), and phosphatidylserine (PS or GPSer).

Sphingolipids are a complicated family of compounds that share a common structural feature, a sphingoid base backbone that is synthesized de novo from the amino acid serine and a long-chain fatty acyl CoA, then converted into ceramides, phosphosphingolipids, glycosphingolipids, and other compounds. The major sphingoid base of mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms. The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

In animals, when there is an oversupply of dietary carbohydrate, excess carbohydrate is converted to triglycerides. This involves the synthesis of fatty acids from acetyl-CoA and the esterification of fatty acids in the production of triglycerides, a process called lipogenesis. Fatty acids are made by fatty acid synthases that polymerize and then reduce acetyl-CoA units. The acyl chains in the fatty acids are extended by a cycle of reactions that add the acetyl group, reduce it to an alcohol, dehydrate it to an alkene group and then reduce it again to an alkane group.

The enzymes of fatty acid biosynthesis are divided into two groups—in animals and fungi all the fatty acid synthase reactions are carried out by a single multifunctional fatty acid synthase protein, while in plant plastids and bacteria separate enzymes perform each step in the pathway. The fatty acids may be subsequently converted to triglycerides that are packaged in lipoproteins and secreted from the liver.

The synthesis of unsaturated fatty acids involves a desaturation reaction, whereby a double bond is introduced into the fatty acyl chain. For example, in humans, the desaturation of stearic acid by stearoyl-CoA desaturase-1 produces oleic acid. The doubly unsaturated fatty acid linoleic acid as well as the triply unsaturated α-linolenic acid cannot be synthesized in mammalian tissues, and are therefore essential fatty acids and must be obtained from the diet.

In eukaryotes, triglyceride synthesis takes place in the endoplasmic reticulum by metabolic pathways in which acyl groups in fatty acyl-CoAs are transferred to the hydroxyl groups of glycerol-3-phosphate and diacylglycerol.

Terpenes and isoprenoids, including the carotenoids, are made by the assembly and modification of isoprene units donated from the reactive precursors isopentenyl pyrophosphate and dimethylallyl pyrophosphate. These precursors can be made in different ways. In animals and archaea, the mevalonate pathway produces these compounds from acetyl-CoA, while in plants and bacteria the non-mevalonate pathway uses pyruvate and glyceraldehyde 3-phosphate as substrates. One important reaction that uses these activated isoprene donors is steroid biosynthesis. Here, the isoprene units are joined together to make squalene and then folded up and formed into a set of rings to make lanosterol. Lanosterol can then be converted into other steroids such as cholesterol and ergosterol.

The technology encompasses any biological molecule (e.g., a lipid, a protein, a small molecule, a hormone, etc.) comprising a non-β-oxidizable fatty acid. For example, the technology encompasses a biological molecule that is covalently linked to a non-β-oxidizable fatty acid, that is bound to a non-β-oxidizable fatty acid, that is attached by a linker to a non-β-oxidizable fatty acid, or that is otherwise physically or chemically associated with a non-β-oxidizable fatty acid. In particular, the technology relates to biological molecules comprising a non-β-oxidizable fatty acid wherein the biological molecule is isolated from a living organism. In some embodiments, the non-β-oxidizable fatty acid is TTA, e.g., that is provided in the culture medium (e.g., as an energy source, as a carbon source, as a nutrient, as an additive, etc.) in which the living organism is grown.

Polar Moiety

Particular embodiments relate to phospholipids comprising a non-β-oxidizable fatty acid such as TTA. Phospholipids according to the technology are not limited in the polar headgroup of the phospholipid. For example, the polar head group may be the polar head group of any suitable lipid.

In some embodiments, the phospholipid is a neutral or anionic phospholipid. For example, in some embodiments the polar head group is the polar head group of, or is derived from, a lipid such as a phospholipid, ceramide, triacylglycerol, lysophospholipid, phosphatidylserine, glycerol, alcohol, alkoxy compound, monoacylglycerol, ganglioside, sphingomyelin, cerebroside, phosphatidylcholine (e.g., dioleoylphosphatidylcholine (DOPC)), phosphatidylethanolamine (e.g., dioleoylphosphatidylethanolamine (DOPE)), phosphatidylinositol, diacylglycerol, phosphatidic acid, glycerocarbohydrate, polyalcohol, and/or phosphatidylglycerol.

Exemplary polar headgroups are, e.g.:

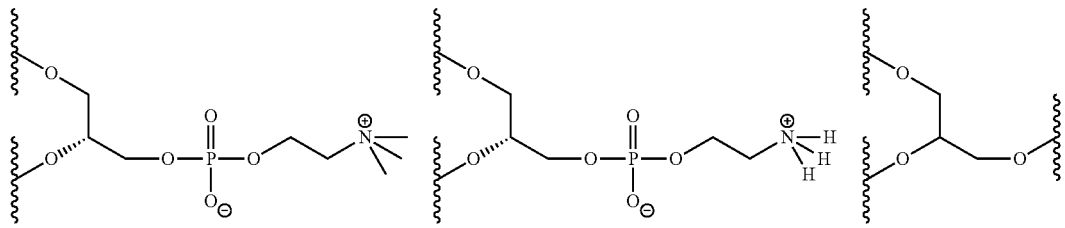

-continued

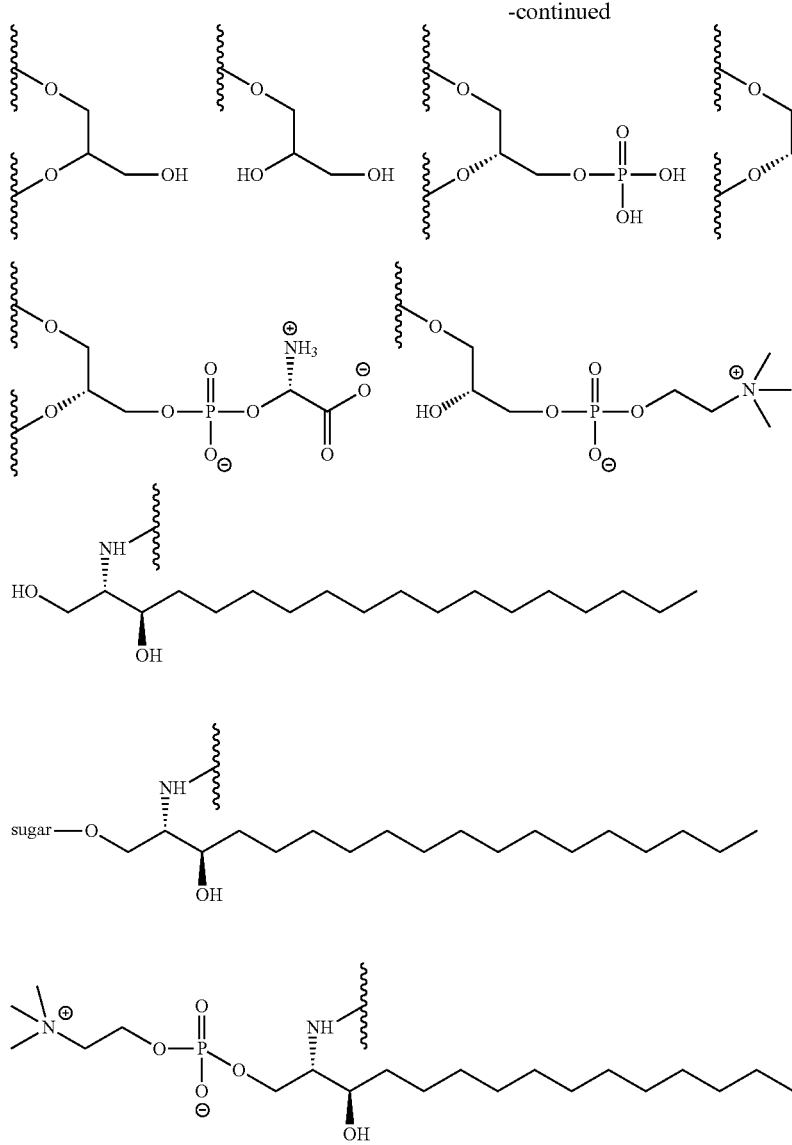

In some embodiments, the polar head group is, or is derived from, a triacylglycerol, e.g., having the structure

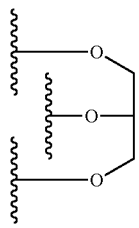 [SMILES: *OCC(CO*)O*]

In some embodiments, the polar head group (PHG) comprises the group

-W-Linker-HG wherein W is selected from $CH_2$, O, $NR^1$, and S, wherein $R^1$ is H or a hydrocarbyl group, wherein Linker is an optional linker group, and HG is a head group.

The head group (HG) may be polar or non-polar. When HG is non-polar it may be rendered polar by group —C(O)W-Linker-. Such head groups are encompassed by the present definition provided —C(O)W-Linker-HG is polar and HG is polar when attached to the —C(O)W-Linker- group.

In some embodiments, the head group (HG) may be an alkyl group, e.g., having at least 5 carbons. In some embodiments, it is a $C_{5-100}$ alkyl group, a $C_{5-80}$ alkyl group, a $C_{5-60}$ alkyl group, a $C_{5-50}$ alkyl group, a $C_{5-40}$ alkyl group, $C_{5-30}$ alkyl group, or a $C_{5-20}$ alkyl group.

For example, in some embodiments the HG is the head group of, or is derived from, a lipid such as a phospholipid, ceramide, triacylglycerol, lysophospholipid, phosphatidylserine, glycerol, alcohol, alkoxy compound, monoacylglycerol, ganglioside, sphingomyelin, cerebroside, phosphatidylcholine, phosphatidylethanolamine, phosphatidylinositol, diacylglycerol, phosphatidic acid, glycerocarbohydrate, polyalcohol, and/or a phosphatidylglycerol.

Exemplary head groups are, e.g.:

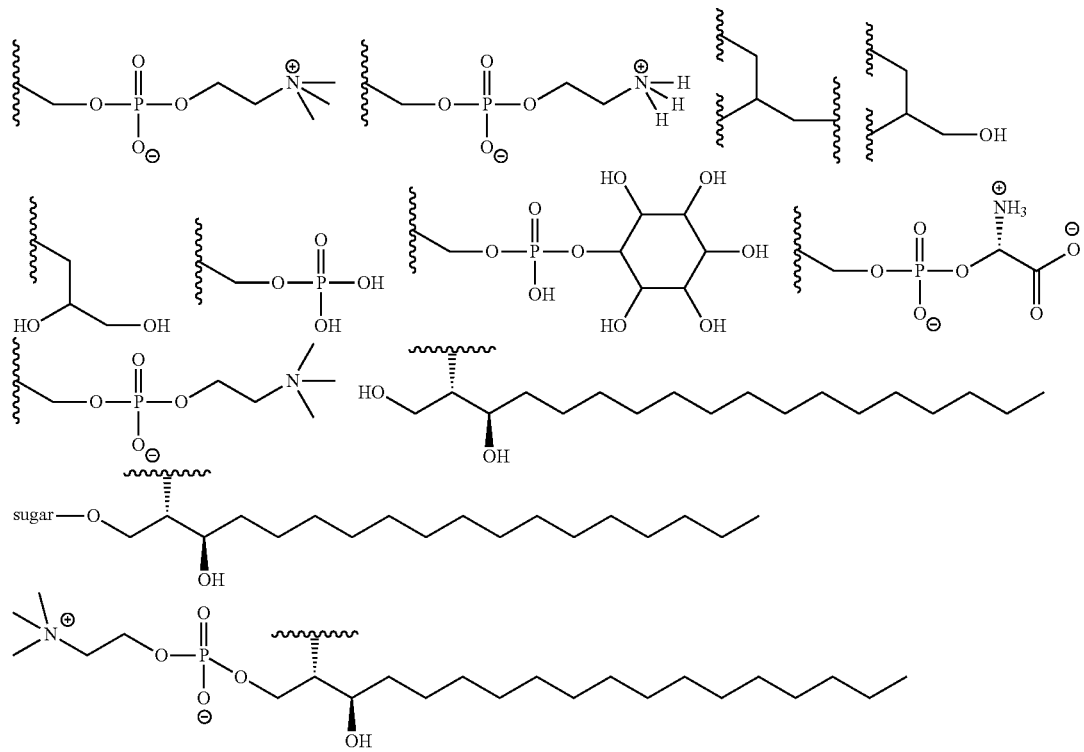

In embodiments comprising a Linker group, the Linker of may be any suitable group. A typical Linker group is a hydrocarbyl group. The term "hydrocarbyl group" as used herein means a group comprising at least C and H and that may optionally comprise one or more other suitable substituents. Examples of such substituents may include halo, alkoxy, nitro, an alkyl group, a cyclic group, etc. In addition to the possibility of the substituents being a cyclic group, a combination of substituents may form a cyclic group. If the hydrocarbyl group comprises more than one C, then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulfur, nitrogen, and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In some embodiments, the Linker is a $C_{1-30}$, $C_{1-25}$, $C_{1-20}$, $C_{1-15}$, $C_{1-10}$, or $C_{1-5}$ hydrocarbyl group; a $C_{1-30}$, $C_{1-25}$, $C_{1-20}$, $C_{1-15}$, $C_{1-10}$, or $C_{1-5}$ hydrocarbon group; a $C_{1-30}$, $C_{1-25}$, $C_{1-20}$, $C_{1-15}$, $C_{1-10}$, or $C_{1-5}$ optionally substituted alkyl group; or a $C_{1-30}$, $C_{1-25}$, $C_{1-20}$, $C_{1-15}$, $C_{1-10}$, or $C_{1-5}$ unsubstituted alkyl group. In some embodiments, at least one optional Linker or no optional Linker groups are present. When one or more or all optional linker groups are not present, the group/compound from which the polar head group is derived is typically chosen to have one or more —OH groups. These allow a simple ester bond between the non-polar moiety and the polar moiety to be provided.

It will be appreciated by one skilled in the art that when an optional Linker is present, two or more W groups may or may not be bonded to the same atom of the linker. It is envisaged that in some embodiments the two or more W groups are boned to different atoms of a linker.

W is selected from $CH_2$, O, $NR^1$, and S, wherein $R^1$ is H, a hydrocarbyl group, a hydrocarbon group, an optionally substituted alkyl group, or an unsubstituted alkyl group, wherein the hydrocarbyl group, hydrocarbon group, optionally substituted alkyl group, and/or unsubstituted alkyl group may be a $C_{1-30}$, $C_{1-25}$, $C_{1-20}$, $C_{1-15}$, $C_{1-10}$, $C_{1-5}$, or $C_{5-15}$ group.

The technology provides in some embodiments a lipid compound comprising at least one non-polar moiety and a polar moiety, wherein each or at least one non-polar moiety is of the formula X—Y—Z—, wherein X is a hydrocarbyl chain; Y is S, Se, $SO_2$, SO, or O; and Z is an optional hydrocarbyl group, wherein the polar moiety is of the formula —[C(O)]$_m$PHG, wherein PHG is a polar head group, and wherein m is the number of non-polar moieties.

In some embodiments, the lipids comprise more than one non-polar moiety, wherein at least one non-polar moiety is of the formula X—Y—Z—, (wherein X is a hydrocarbyl chain; Y is S, Se, $SO_2$, SO, or O; and Z is an optional hydrocarbyl group) and one or more lipids which are not of this formula. In other words, technology includes lipids which have multiple non-polar moieties of which only one has the structure X—Y—Z—.

In some embodiments, the lipids comprise at least two non-polar moieties and a polar moiety, wherein one non-polar moiety is of the formula X—Y—Z—, wherein one non-polar moiety is of the formula X—CH$_2$—Z—, wherein each X is independently a hydrocarbyl chain; Y is S, Se, SO$_2$, SO, or O; and each Z is independently an optional hydrocarbyl group, wherein the chain X—CH$_2$—Z optionally contains an even number of atoms; wherein the polar moiety is of the formula —[C(O)]$_m$PHG, wherein PHG is a polar head group, and wherein m is the number of non-polar moieties.

The chain length of X—CH$_2$— is the longest chain of directly bonded atoms within moiety X—CH$_2$. A chain and consequently the chain length do not include atoms of cyclic substituents or substituents of a terminal carbon.

In some embodiments, each non-polar moiety is of the formula X—Y—Z—, wherein X is a hydrocarbyl chain; Y is S, Se, SO$_2$, SO, or O; and Z is an optional hydrocarbyl group.

As discussed above X is a hydrocarbyl chain. By "hydrocarbyl chain" it is meant a linear hydrocarbyl group. In the following definitions of chain length it is meant the longest chain of directly bonded atoms within moiety X. A chain and consequently the chain length do not include atoms of cyclic substituents or substituents of a terminal carbon. In some embodiments, X is an optionally substituted alkyl, optionally substituted alkenyl, or optionally substituted alkynyl. In some embodiments, X is an optionally substituted $C_6$-$C_{24}$ alkyl, optionally substituted $C_6$-$C_{24}$ alkenyl, or optionally substituted $C_8$-$C_{24}$ alkynyl. In some embodiments, X is an optionally substituted alkyl having a chain length of 6 to 24 atoms, optionally substituted alkenyl having a chain length of 6 to 24 atoms, or optionally substituted alkynyl having a chain length of 6 to 24 atoms. In some embodiments, X is an optionally substituted alkyl having a chain length of 10 to 18 atoms, optionally substituted alkenyl having a chain length of 10 to 18 atoms, or optionally substituted alkynyl having a chain length of 10 to 18 atoms. In some embodiments, X is an optionally substituted alkyl having a chain length of 14 atoms, optionally substituted alkenyl having a chain length of 14 atoms, or an optionally substituted alkynyl having a chain length of 14 atoms, for example, in some embodiments X is an unsubstituted alkyl, unsubstituted alkenyl, or an unsubstituted alkynyl.

In some embodiments, X is an unsubstituted $C_6$-$C_{24}$ alkyl, unsubstituted $C_6$-$C_{24}$ alkenyl, or an unsubstituted $C_6$-$C_{24}$ alkynyl, e.g., X is an unsubstituted alkyl having a chain length of 6 to 24 atoms, unsubstituted alkenyl having a chain length of 6 to 24 atoms, or an unsubstituted alkynyl having a chain length of 6 to 24 atoms.

In some embodiments, X is an unsubstituted $C_{10}$-$C_{18}$ alkyl, unsubstituted $C_{10}$-$C_{18}$ alkenyl, or an unsubstituted $C_{10}$-$C_{18}$ alkynyl, e.g., X is an unsubstituted alkyl having a chain length of 10 to 18 atoms, unsubstituted alkenyl having a chain length of 10 to 18 atoms, or an unsubstituted alkynyl having a chain length of 10 to 18 atoms. In some embodiments, X is an unsubstituted $C_{14}$ alkyl, unsubstituted $C_{14}$ alkenyl, or an unsubstituted $C_{14}$ alkynyl, e.g., X is an unsubstituted alkyl having a chain length of 14 atoms, unsubstituted alkenyl having a chain length of 14 atoms, or an unsubstituted alkynyl having a chain length of 14 atoms.

In some embodiments, X is a hydrocarbon chain By "hydrocarbon chain" it is meant a linear hydrocarbon group. For example, in some embodiments X a $C_6$-$C_{24}$ alkenyl containing one or more double bonds and optionally one or more triple bonds, $C_6$-$C_{24}$ alkynyl, $C_6$-$C_{24}$ alkyl optionally substituted with at least one of F, Cl, hydroxy, $C_1$-$C_4$ alkoxy, $C_1$-$C_4$ alkylthio, $C_2$-$C_5$ acyloxy, or $C_1$-$C_4$ alkyl. One skilled in the art will appreciate that alkynyl groups containing one or more alkenyl groups may be provided or alkenyl groups containing one or more alkynyl groups may be provided When X contains one or more double bonds, some embodiments provide that at least one double bond is in cis configuration. Some embodiments provide that all double bonds are in cis configuration.

In one preferred aspect X is an acetylenic hydrocarbyl group. The term "acetylenic hydrocarbyl" as used herein means a group comprising at least C and H, having at least one —C≡C— bond and may optionally comprise one or more other suitable substituents. Examples of such substituents may include halo, alkoxy, nitro, a hydrocarbon group, an N-acyl group, a cyclic group, etc. In addition to the possibility of the substituents being a cyclic group, a combination of substituents may form a cyclic group. If the hydrocarbyl group comprises more than one C, then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulfur, nitrogen, and oxygen.

In some embodiments, X is an acetylenic hydrocarbyl group containing a single —C≡C— bond, e.g., X contains one and only one —C≡C— bond. In some embodiments, the acetylenic hydrocarbyl group is an alkynyl group. In some embodiments, X is an optionally substituted alkynyl group having a chain length of 6 to 24 atoms, X is an optionally substituted alkynyl group having a chain length of 10 to 18 atoms, X is an optionally substituted alkynyl groups having a chain length of 16 or 17 atoms, or X is an optionally unsubstituted alkynyl group. For example, in some embodiments, X is an unsubstituted $C_6$-$C_{24}$ alkynyl group. In some embodiments, X is an unsubstituted alkynyl group having a chain length of 6 to 24 atoms, X is an unsubstituted $C_{10}$-$C_{18}$ alkynyl group, X is an unsubstituted alkynyl groups having a chain length of 10 to 18 atoms; X is an unsubstituted $C_{16}$ or $C_{17}$ alkynyl group, X is an unsubstituted alkynyl having a chain length of 16 or 17 atoms. In some embodiments, the —C≡C— of the acetylenic hydrocarbyl group is distanced from the terminal end of the acetylenic hydrocarbyl group by from 2 to 15 carbons, e.g., by 2 carbons, by 3 carbons, by 7 carbons, or by 13 carbons.

In some embodiments, at least one Y group is S or Se, e.g., in some embodiments each Y is selected from S and Se. Some embodiments provide that at least one Y group is S and some embodiments provide that each Y is S.

In some embodiments, the present invention provides structured phospholipid compositions comprising phospholipid molecules of the following structure:

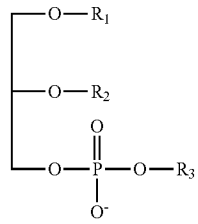

wherein one of R1 and R2 is a non-beta-oxidizable fatty acid analogue moiety and the other of R1 and R2 is a bioactive fatty acid moiety selected from the group consisting of an omega-3 fatty acid moiety, on omega-6 fatty acid moiety, a conjugated linoleic fatty acid moiety, a sciadonic fatty acid moiety, and combinations thereof. The compositions of the present invention may comprise 99.5% 99.9% or 100% of the structured phospholipid, or may be compositions comprising a mixture of phospholipid molecules that can be characterized based on the molar percentage of fatty acid moieties present in the composition as a whole. In some embodiments, the composition comprises greater than 50%, 80%, 90% or 99% on a molar basis of said non-beta-oxidizable fatty acid analogue moiety at position R1. In some embodiments, the composition comprises greater than 50%, 80%, 90% or 99% on a molar basis of said non-beta-oxidizable fatty acid analogue moiety at position R2. In some embodiments, the composition comprises greater than about 50%, 80%, 90% or 99% on a molar basis of said bioactive fatty acid moieties or combinations thereof at position R2. In some embodiments, the composition comprises greater than about 50%, 80%, 90% or 99% on a molar basis of said bioactive fatty acid moiety at position R1. In some embodiments, the bioactive fatty acid moiety is selected from the group consisting of EPA, DHA and a combination thereof. In some embodiments, the composition comprises the bioactive fatty acid moiety is EPA. In some embodiments, the composition comprises the bioactive fatty acid moiety is DHA. In some embodiments, the composition comprises the bioactive fatty acid moiety is conjugated linoleic acid. In some embodiments, the composition comprises the bioactive fatty acid moiety is sciadonic acid. In some embodiments, R3 is selected from a —H or nitrogen containing compound choline (HOCH$_2$CH$_2$N$^+$(CH$_3$)$_3$OH$^-$), ethanolamine (HOCH$_2$CH$_2$NH$_2$), serine, inositol such as cyclohexane polyoinositol and derivatives thereof.

Acylation of sn-glycero-3-phosphocholine (GPC) with an activated fatty acid, such as fatty acid imidazolides, is a standard procedure in phosphatidylcholine synthesis. It is usually carried out in the presence of DMSO anion with DMSO as solvent (Hermetter; Chemistry and Physics of lipids, 1981, 28, 111). Sn-Glycero-3-phosphocholine, as cadmium (II) adduct can also be reacted with the imidazolide activated fatty acid in the presence of DBU (1,8-diazabicyclo[5.4.0]undec-7-ene) to prepare the phosphatidylcholine of the respective fatty acid (International application number PCT/GB2003/002582). Enzymatic transphosphatidylation can affect the transformation of phosphatidylcholine to phosphatidyletanolamine (Wang et al, J. Am. Chem. Soc., 1993, 115, 10487). In other embodiments, a lysophospholipid with a desired bioactive fatty acid moiety (e.g., omega-3 fatty acid moiety, conjugated linoleic acid moiety of sciadonic acid moiety) at the SN-1 or SN-2 position is acylated with a non-beta-oxidizable fatty acid analogue moiety by combining desired omega-3 fatty acid non-beta-oxidizable fatty acid analogue moiety anhydride (e.g. from TTA) and 4-pyrrolidinopyridine as a catalyst (1.2 equivalents) in alcohol-free chloroform. Polyunsaturated fatty acids containing phospholipids may be prepared by various ways, mainly by chemical synthesis of phospholipids as described, by enzymatic esterification and transesterification of phospholipids or enzymatic transphosphatidylation of phospholipids. (Hosokawa, J. Am. Oil Chem. Soc. 1995, 1287, Lilja-Hallberg, Biocatalysis, 1994, 195).

Exemplary Embodiments of Compounds

Examples of embodiments according to the technology are:

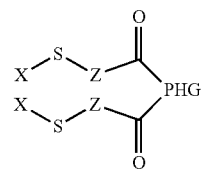

wherein groups X and Z are selected independently of each other;

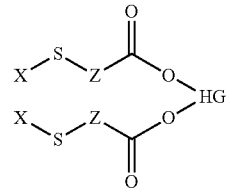

wherein groups X and Z are selected independently of each other.

Z is an optional hydrocarbyl group. In some embodiments, Z is present and in some embodiments, Z is not present. In some embodiments, Z is an alkyl group such as $C_1$-$C_{10}$, $C_1$-$C_6$, or a $C_1$-$C_3$ alkyl group such as, e.g., —CH$_2$—.

In some embodiments, Y and Z together may be formed by a unit that repeats within the YZ moiety. For example, in some embodiments Y—Z together represent the group $[Y^1$—CH$_2]_n$, wherein $Y^1$ is S, Se, SO$_2$, SO, or O, and wherein n is an integer from 1 to 20. In some embodiments, Y is Se or S, e.g., Y is S, and n is from 1 to 10, e.g., 1 to 5 or 1, 2 or 3, e.g., in some embodiments, n is 1.

Some embodiments provide a compound having the structure

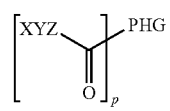

wherein p is at least 1, such as 1 to 1000; 1 to 100; 1 to 50; 1 to 20; 1 to 10; 1 to 5; e.g., 1, 2 or 3; and wherein each W, X, Y, and Z is selected independently of each other. Examples of compounds from which the polar head group may be derived for given values of p are provided in Table I:

TABLE 1

| p | |
|---|---|
| 1 | glycerols |
|   | alcohols |
|   | alkoxy compounds |
|   | lysophospholipids |
|   | monoacylglycerols |
|   | gangliosides |
|   | sphingomyelins |
|   | cerebrosides |
| 2 | phosphatidylcholines (PC) |
|   | phosphatidylethanolamines (PE), |
|   | phosphatidylserines (PS) |
|   | phosphatidylinositols (PI) |
|   | diacylglycerols |

TABLE 1-continued
| p | |
|---|---|
| | Phosplatidic acids |
| | glycerocarbohydrates |
| | phosphatidylglycerols |
| 3 | triacylglycerols |
| 1 or more | polyalcohols |
For example, embodiments of the technology provide compounds having formulas as follows:
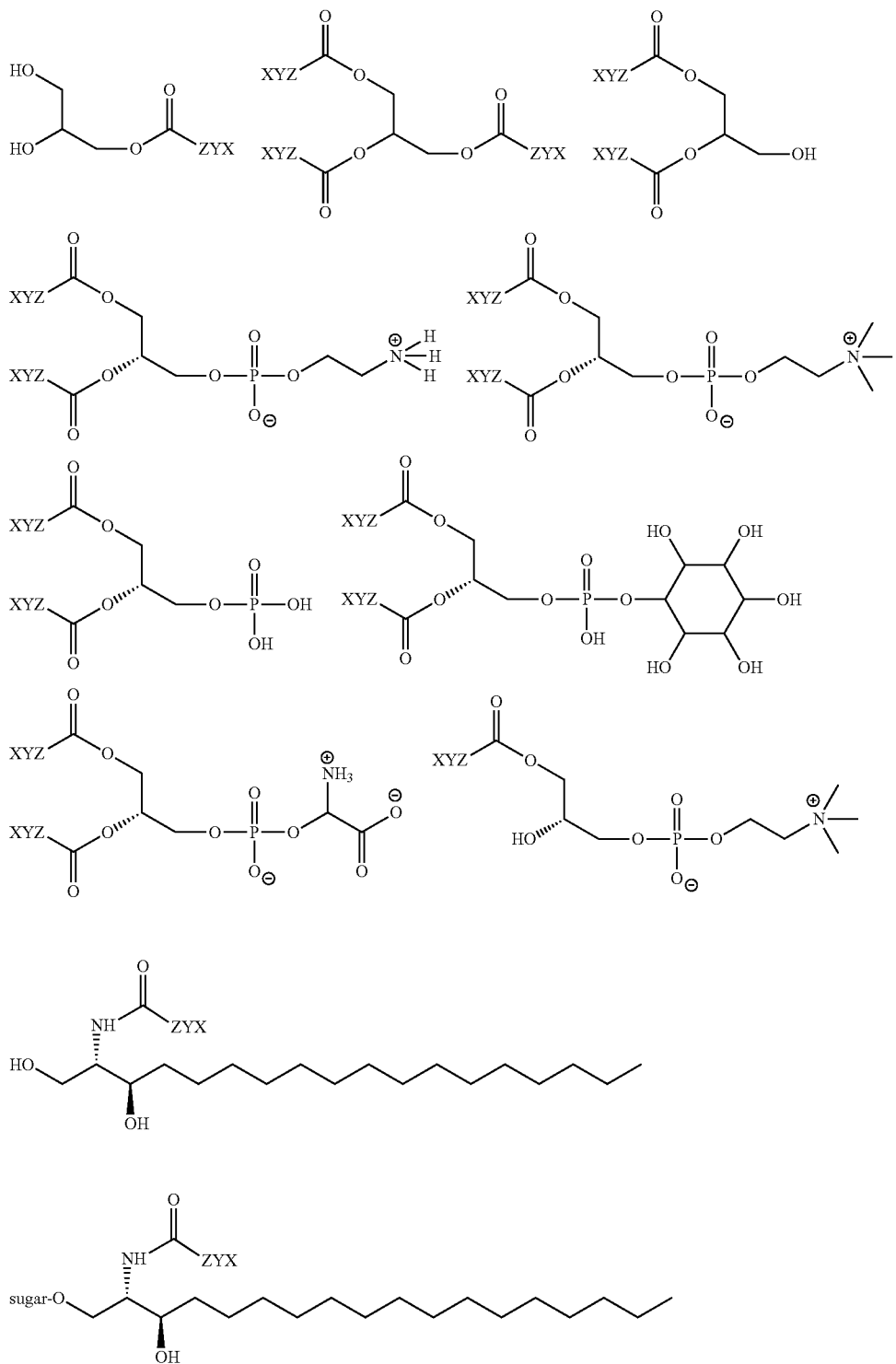

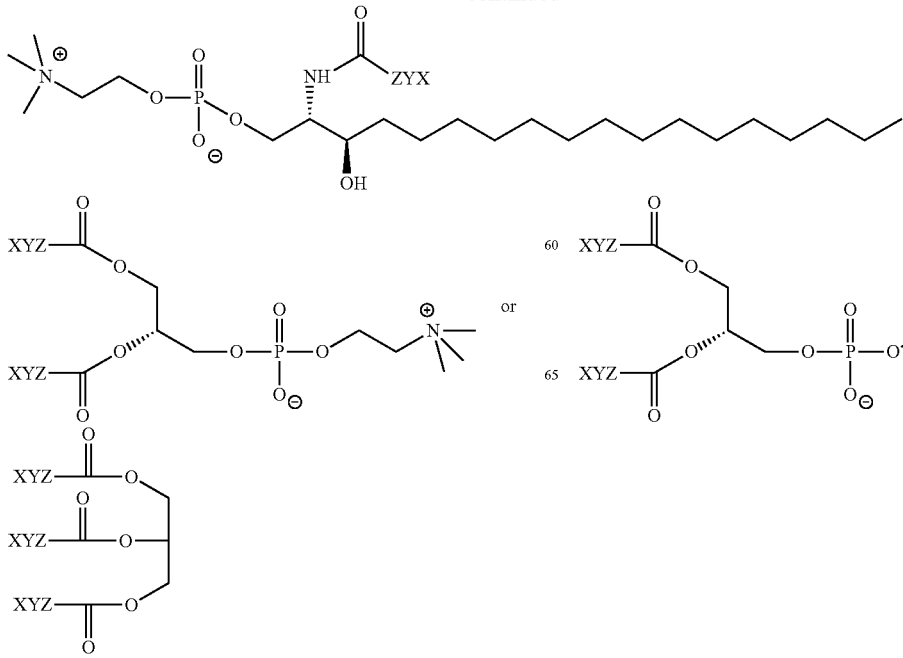

Some embodiments provide a compound having the structure

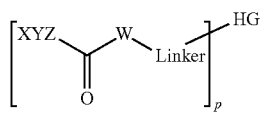

wherein p is 1 to 10, e.g., 1 to 5; e.g., 1, 2 or 3, and wherein each W, X, Y, and Z is selected independently of each other.

Embodiments provide compounds having a structure such as

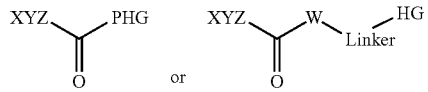

In some embodiments, the compound comprises at least two non-polar moieties wherein each is independently selected from non-polar moieties of the formula X—Y—Z—.

Some embodiments provide a compound having a formula as follows

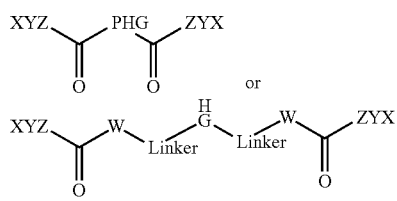

wherein each W, X, Y, and Z is selected independently of each other.

In some embodiments, the compound comprises at least three non-polar moieties wherein each is independently selected from non-polar moieties of the formula X—Y—Z—. For example, some embodiments of the technology provide a compound having a structure of

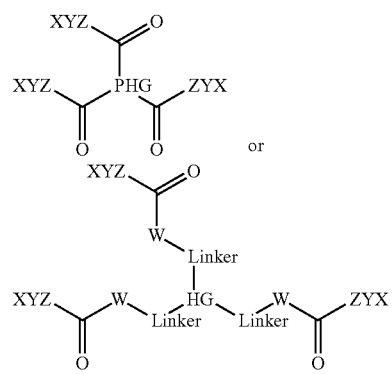

wherein each W, X, Y and Z is selected independently of each other.

Some embodiments provide a compound having a structure defined as

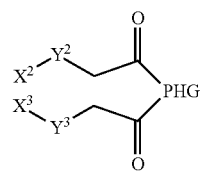

wherein $Y^2$ and $Y^3$ are independently S or Se (e.g., $Y^2$ and $Y^3$ are each S), and $X^2$ and $X^3$ are independently an unsubstituted $C_{10}$-$C_{18}$ alkyl, unsubstituted $C_{10}$-$C_{18}$ alkenyl, and/or an unsubstituted $C_{10}$-$C_{18}$ is alkynyl (e.g., $X^2$ and $X^3$ are independently an unsubstituted $C_{14}$ alkyl, unsubstituted $C_{14}$ alkenyl, and/or an unsubstituted $C_{14}$ alkynyl). In some embodiments, $Y^2$ and $Y^3$ are each S and/or $X^2$ and $X^3$ are independently $CH_3(CH_2)_{13}$—, $CH_3(CH_2)_6CH$=$CH(CH_2)_5$—, and/or $CH_3CH_2C\equiv C(CH_2)_{10}$—; in some embodiments, $X^2$ and $X^3$ are both $CH_3(CH_2)_{13}$—; in some embodiments, $X^2$ and $X^3$ are both $CH_3(CH_2)_6CH$=$CH(CH_2)_5$—; and in some embodiments, $X^2$ and $X^3$ are both $CH_3CH_2C\equiv C(CH_2)_{10}$—. In some embodiments, the PHG is derived from the polar head group of a phosphatidylcholine or a phosphatidylethanolamine.

In some embodiments, the technology provides a compound having the structure

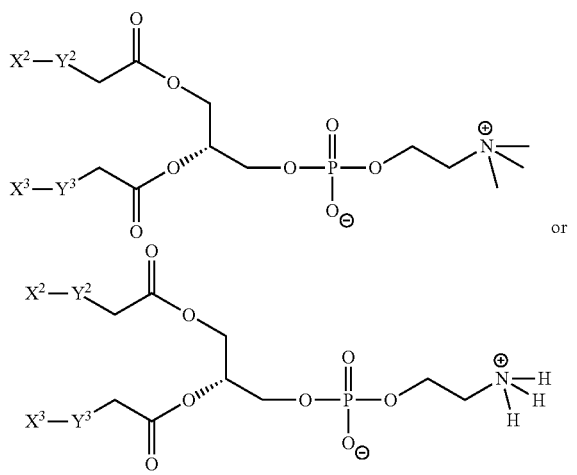

wherein $Y^2$ and $Y^3$ are independently S or Se and/or $X^2$ and $X^3$ are independently $C_{10}$-$C_{18}$ alkyl, $C_{10}$-$C_{18}$ alkenyl, and/or $C_{10}$-$C_{18}$ alkynyl. In some embodiments, $Y^2$ and $Y^3$ are independently S or Se and/or $X^2$ and $X^3$ are independently unsubstituted $C_{10}$-$C_{18}$ alkyl, $C_{10}$-$C_{18}$ alkenyl, or $C_{10}$-$C_{18}$ alkynyl, e.g., $Y^2$ and $Y^3$ are independently S or Se and/or $X^2$ and $X^3$ are independently unsubstituted $C_{14}$ alkyl, $C_{14}$ alkenyl, and/or $C_{14}$ alkynyl. In some embodiments, $Y^2$ and $Y^3$ are each S and/or $X^2$ and $X^3$ are both $CH_3(CH_2)_{13}$—, $X^2$ and $X^3$ are both $CH_3(CH_2)_6CH$=$CH(CH_2)_5$—, or $X^2$ and $X^3$ are both $CH_3CH_2C\equiv C(CH_2)_{10}$—.

In some embodiments, the compounds of the technology have a structure according to

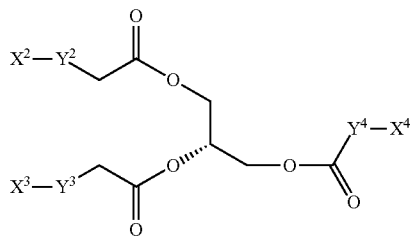

wherein Y2, $Y^3$, and $Y^4$ are independently S or Se and/or $X^2$, $X^3$, and $X^4$ are independently a $C_{10}$-$C_{18}$ alkyl, $C_{10}$-$C_{18}$ alkenyl, and/or a $C_{10}$-$C_{18}$ alkynyl. For example, in some embodiments, Y2, $Y^3$, and $Y^4$ are independently S or Se and/or $X^2$, $X^3$, and $X^4$ are independently a $C_{14}$ alkyl, $C_{14}$ alkenyl, and/or a $C_{14}$ alkynyl. In some embodiments, Y2, $Y^3$, and $Y^4$ are each S and/or $X^2$, $X^3$, and $X^4$ are independently a $C_{10}$-$C_{18}$ alkyl, $C_{10}$-$C_{18}$ alkenyl, and/or a $C_{10}$-$C_{18}$ alkynyl. In some embodiments, Y2, $Y^3$, and $Y^4$ are each S and/or $X^2$, $X^3$, and $X^4$ are independently an unsubstituted $C_{10}$-$C_{18}$ alkyl, an unsubstituted $C_{10}$-$C_{18}$ alkenyl, and/or an unsubstituted $C_{10}$-$C_{18}$ alkynyl. In some embodiments, Y2, $Y^3$, and $Y^4$ are each S and/or $X^2$ and $X^3$ are independently a $C_{14}$ alkyl, $C_{14}$ alkenyl, and/or a $C_{14}$ alkynyl. In some embodiments, Y2, $Y^3$, and $Y^4$ are each S and/or $X^2$, $X^3$, and $X^4$ are each $CH_3(CH_2)_{13}$—; in some embodiments, Y2, $Y^3$, and $Y^4$ are each S and/or $X^2$, $X^3$, and $X^4$ are each $CH_3(CH_2)_6CH$=$CH(CH_2)_5$—; in some embodiments, Y2, $Y^3$, and $Y^4$ are each S and/or $X^2$, $X^3$, and $X^4$ are each $CH_3CH_2C\equiv C(CH_2)_{10}$—.

In some embodiments, in any of these compounds ester linkages between lipid tails and the glycerol moiety are replaced by ether linkages.

Further Aspects

In some embodiments, the compounds provided herein are combined with a liposome or formulated into a micellar form to assist in administration. In some embodiments, compounds are formulated in a cochleate delivery vehicle. Cochleate delivery vehicles are a new technology platform for oral delivery of drugs. Cochleates are stable phospholipid-cation precipitates composed of simple, naturally occurring materials, for example, phosphatidylserine and calcium. Cochleates are a potential nanosized system that can encapsulate hydrophobic, amphiphilic, negatively, or positively charged moieties.

In some embodiments, the compound is an isolated form or purified form. For example, the compound may be in a form or at a purity other than that found in a biological system such as in vivo. In some embodiments, the compound is semi-isolated or semi-purified, e.g., the compound is an isolated form or purified form and is present in a composition with one or more other biological molecules that are not contaminants or impurities. In some embodiments, the compounds provided are formulated to provide a pharmaceutical composition comprising a compound according to the technology and/or a pharmaceutically acceptable carrier, diluent, excipient, or adjuvant.

An addition, embodiments provide compounds that are lipids comprising at least one non-polar moiety and a polar moiety, wherein the non-polar moiety is of the formula X—Y—Z—, wherein X is a hydrocarbyl chain; Y is S, Se, $SO_2$, SO, O, or $CH_2$; and Z is an optional hydrocarbyl group. Furthermore, when Y is $CH_2$, the chain X—Y—Z contains an even number of atoms, the polar moiety is —[C(O)]$_m$PHG, wherein PHG is a polar head group and m is the number of non-polar moieties.

Pharmaceutical Compositions

Provided herein are pharmaceutical compositions comprising a therapeutically effective amount of an agent according to the present technology and a pharmaceutically acceptable carrier, diluent, or excipient (including combinations thereof).

A composition according to the technology comprises or consists of a therapeutically effective amount of a pharmaceutically active agent. In some embodiments, it includes a pharmaceutically acceptable carrier, diluent, or excipient (including combinations thereof). Acceptable carriers or diluents for therapeutic use are well known in the pharmaceutical art and are described, for example, in Remington's Pharmaceutical Sciences, Mack Publishing Co. (A. R. Gennaro edit. 1985). The choice of pharmaceutical carrier, excipient, or diluent is selected with regard to the intended route of administration and standard pharmaceutical practice. The pharmaceutical comprise as, or in addition to, the carrier, excipient, or diluent any suitable binder(s), lubricant(s), suspending agent(s), coating agent(s), and/or solubilizing agent(s).

This pharmaceutical composition will desirably be provided in a sterile form. It may be provided in unit dosage form and will generally be provided in a sealed container. A plurality of unit dosage forms may be provided.

Pharmaceutical compositions within the scope of the present technology may include one or more of the following: preserving agents, solubilizing agents, stabilizing agents, wetting agents, emulsifiers, sweeteners, colorants, flavoring agents, odorants, and/or salts. Compounds of the present technology may themselves be provided in the form of a pharmaceutically acceptable salt. In addition, embodiments may comprise buffers, coating agents, antioxidants, suspending agents, adjuvants, excipients, and/or diluents. Examples of preservatives include sodium benzoate, sorbic acid, and esters of p-hydroxybenzoic acid.

They may also contain other therapeutically active agents in addition to compounds of the present technology. Where two or more therapeutic agents are used they may be administered separately (e.g., at different times and/or via different routes) and therefore do not always need to be present in a single composition. Thus, combination therapy is within the scope of the present technology.

Route of Administration

A pharmaceutical composition within the scope of the present technology may be adapted for administration by any appropriate route. For example, it may be administered by the oral (including buccal or sublingual), rectal, nasal, topical (including buccal, sublingual, or transdermal), vaginal, or parenteral (including subcutaneous, intramuscular, intravenous, or intradermal) routes. Such a composition may be prepared by any method known in the art of pharmacy, for example, by admixing one or more active ingredients with a suitable carrier.

In various embodiments, different drug delivery systems are used to administer pharmaceutical compositions of the present technology, depending upon the desired route of administration. Drug delivery systems are described, for example, by Langer (*Science* 249:1527-1533 (1991)) and by Illum and Davis (*Current Opinions in Biotechnology* 2: 254-259 (1991)).

The agents of the present technology may be administered alone but will generally be administered as a pharmaceutical composition—e.g., the agent is in admixture with a suitable pharmaceutical excipient, diluent, or carrier selected with regard to the intended route of administration and standard pharmaceutical practice. For example, in some embodiments the agent is administered (e.g., orally or topically) in the form of tablets, capsules, ovules, elixirs, solutions, or suspensions, which may contain flavoring or coloring agents, for immediate, delayed, modified, sustained, pulsed, and/or controlled-release applications.

In some embodiments, tablets contain excipients such as microcrystalline cellulose, lactose, sodium citrate, calcium carbonate, dibasic calcium phosphate and/orglycine; disintegrants such as starch (preferably corn, potato, or tapioca starch), sodium starch glycollate, croscarmellose sodium, and/or certain complex silicates; and/or granulation binders such as polyvinylpyrrolidone, hydroxypropylmethylcellulose (HPMC), hydroxypropylcellulose (HPC), sucrose, gelatin, and/or acacia. Additionally, lubricating agents such as magnesium stearate, stearic acid, glyceryl behenate, and talc may be included.

In some embodiments, solid compositions of a similar type are also employed as fillers in gelatin capsules. Examples of excipients in this regard include lactose, starch, a cellulose, milk sugar, or high molecular weight polyethylene glycols. For some embodiments of aqueous suspensions and/or elixirs, the agent is combined with various sweetening or flavoring agents, coloring matter or dyes, with emulsifying and/or suspending agents and with diluents such as water, ethanol, propylene glycol, and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, via the penis, vaginal, epidural, sublingual.

It is to be understood that not all of the agent need be administered by the same route. Likewise, if the composition comprises more than one active component, then those components may be administered by different routes.

If the agent of the present technology is administered parenterally, then examples of such administration include one or more of: intravenously, intra-arterially, intraperitoneally, intrathecally, intraventricularly, intraurethrally, intrastemally, intracranially, intramuscularly, or subcutaneously administering the agent; and/or by using infusion techniques.

Oral Administration

In some embodiments, pharmaceutical compositions adapted for oral administration are provided as capsules or tablets; as powders or granules; as solutions, syrups or suspensions (in aqueous or non-aqueous liquids); as edible foams or whips; or as emulsions. Tablets or hard gelatine capsules may comprise lactose, maize starch or derivatives thereof, stearic acid or salts thereof. Soft gelatine capsules may comprise vegetable oils, waxes, fats, semi-solid, or liquid polyols etc. Solutions and syrups may comprise water, polyols and sugars. For the preparation of suspensions, oils (e.g., vegetable oils) may be used to provide oil-in-water or water-in-oil suspensions. An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Transdermal Administration

Pharmaceutical compositions adapted for transdermal administration may be provided as discrete patches intended to remain in intimate contact with the epidermis of the recipient for a prolonged period of time. For example, the active ingredient may be delivered from the patch by iontophoresis, e.g., as described in *Pharmaceutical Research*, 3: 318 (1986)).

Topical Administration

Alternatively, the agent of the present technology can be administered in the form of a suppository or pessary, or it may be applied topically in the form of a gel, hydrogel, lotion, solution, cream, ointment or dusting powder. The agent of the present technology may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the agent of the present technology can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Rectal Administration

Pharmaceutical compositions adapted for rectal administration may be provided as suppositories or enemas.

Nasal Administration

Pharmaceutical compositions adapted for nasal administration may use solid carriers, e.g., powders (e.g., having a particle size in the range of 20 to 500 microns). Powders can be administered in the manner in which snuff is taken, e.g., by rapid inhalation through the nose from a container of powder held close to the nose. Compositions adopted for nasal administration may alternatively use liquid carriers, e.g., nasal sprays or nasal drops. These may comprise aqueous or oil solutions of the active ingredient. Compositions for administration by inhalation may be supplied in specially adapted devices, e.g., in pressurized aerosols, nebulizers, or insufflators. These devices can be constructed so as to provide predetermined dosages of the active ingredient Vaginal Administration Pharmaceutical compositions adapted for vaginal administration may be provided as pessaries, tampons, creams, gels, pastes, foams or spray formulations.

Parenteral Administration

If the agent of the present technology is administered parenterally, then examples of such administration include one or more of: intravenously, intra-arterially, intraperitoneally, intrathecally, intraventricularly, intraurethrally, intrasternally, intracranially, intramuscularly or subcutaneously administering the agent; and/or by using infusion techniques.

For parenteral administration, the agent is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Transdermal; Transmucosal; Transurethral or Intraurethral

"Transdermal" refers to the delivery of a compound by passage through the skin and into the blood stream. "Transmucosal" refers to delivery of a compound by passage of the compound through the mucosal tissue and into the blood stream. "Transurethral" or "intraurethral" refers to delivery of a drug into the urethra, such that the drug contacts and passes through the wall of the urethra and enters into the blood stream.

Penetration Enhancement or Permeation Enhancement

"Penetration enhancement" or "permeation enhancement" refers to an increase in the permeability of the skin or mucosal tissue to a selected pharmacologically active compound such that the rate at which the compound permeates through the skin or mucosal tissue is increased.

Penetration enhancers may include, for example, dimethylsulfoxide (DMSO); dimethyl formamide (DMF); N,N-dimethylacetamide (DMA); decylmethylsulfoxide (CI-OMSO); polyethyleneglycol monolaurate (PEGML); glyceral monolaurate; lecithin; 1-substituted azacycloheptanones, particularly 1-N-dodecylcyclaza-cycloheptanones (e.g., as available under the trademark Azone™ from Nelson Research & Development Co., Irvine, Calif.), alcohols, and the like.

Carriers or Vehicles

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner Examples of pharmaceutically acceptable carriers include, for example, water, salt solutions, alcohol, silicone, waxes, petroleum jelly, vegetable oils, polyethylene glycols, propylene glycol, sugars, gelatin, lactose, amylose, magnesium stearate, talc, surfactants, silicic acid, viscous paraffin, perfume oil, fatty acid monoglycerides and diglycerides, petroethral fatty add esters, hydroxymethyl-cellulose, polyvinylpyrrolidone, and the like.

Epidermal Drug Delivery (Transfersomes)

Transfersomes ("carrying bodies") are complex, most often vesicular, bi- or multi-component aggregates capable of crossing barriers and of transferring material between the application and the destination sites. Transfersomes are sold by IDEA Corporation, Munich, Germany, and TRANSFERSOME is a trade mark of that company. Transfersome transdermal drug delivery technology may be used for controllable and non-invasive delivery of a wide variety of large molecules as well as for the improved delivery of small molecules, including the metabolic enzyme antagonists and/or drugs of the present technology.

Transfersomes may be optimized to attain extremely flexible and self-regulating membranes. They are therefore deformable and consequently can cross microporous barriers efficiently, even when the available passages are much smaller than the average aggregate size. Transfersome formulations are typically composed of natural amphipathic compounds suspended in a water-based solution, optionally containing biocompatible surfactants. Vesicular Transfersomes consist of a lipid bilayer surrounding an aqueous core and further contain at least one component, capable of softening the membrane. The bilayer of a Transferosome is therefore more flexible than a liposome membrane, even metastable. Transfersome vesicles consequently change their shape easily by adjusting locally to ambient stress.

Skin is one of the best biological barriers. Its outermost part reaches less than 10% into the depth of the skin but contributes over 80% to the skin permeability barrier. This body protecting layer consists of overlapping, flaccid corneocytes, organized in columnar clusters, sealed with multilamellar lipid sheets that are covalently attached to the cell membranes and very tightly packed. Generally, the average number of, and the degree of order in, the intercellular lipid lamellae increases toward the skin surface. This is accompanied by a continuous, but nonlinear, decrease in local water content near the surface. Notwithstanding this, the peak skin barrier is located in the inner half of the outermost layer, where the intercellular lipid seals are already formed, but not yet compromised by the skin cells detachment.

Passage of transfersome aggregates across the skin is a function of vesicle membrane flexibility, hydrophilicity, and the ability to retain vesicle integrity, while the aggregate undergoes a significant change in shape. When a suspension of Transfersome vesicles is placed on the surface of the skin, water evaporates from the relatively arid skin surface and the vesicles start to dry out. Due to the strong polarity of major Transfersome ingredients, the large number of hydrophilic groups on the membrane, assisted by the softness of the membrane, the vesicles are attracted to the areas of higher water content in the narrow gaps between adjoining cells in the skin barrier, enabling skin penetration of the vehicle. This, together with the vesicle's extreme ability to deform, enables Transfersome aggregates to open, temporarily, the tiny "cracks" through which water normally evaporates out of the skin Channels between the skin cells, two orders of magnitude wider than the original micropores, are thus created. Such newly activated passages can accommodate sufficiently deformable vesicles, which maintain their integrity but change their shape to fit the channel Along the resulting "virtual pathways", or "virtual channels" in the outermost layer, Transfersomes reach regions of high water content in the deeper skin layers. There, the vesicles (re) distribute. Since Transfersomes are too large to enter the blood vessels locally, they bypass the capillary bed and get to subcutaneous tissue, where they accumulate.

Although small molecules that have crossed the outermost layer of the skin (stratum corneum) are normally cleared from the skin through the blood circulation, delivery of drugs by means of Transfersome vesicles allows accumulation of drug deep under the skin. Due to their large size, the vesicles are cleared slowly from the skin and associated drugs can accumulate at the site. Transfersome mediated administration of weight drugs, consequently, tends to shift the drug distribution towards the deep tissue under the application site.

Blood Brain Barrier (BBB)

Pharmaceutical compositions may be designed to pass across the blood brain barrier (BBB). For example, a carrier such as a fatty acid, inositol or cholesterol may be selected that is able to penetrate the BBB. The carrier may be a substance that enters the brain through a specific transport system in brain endothelial cells, such as insulin-like growth factor I or II. The carrier may be coupled to the active agent or may contain and/or be in admixture with the active agent. Liposomes can be used to cross the BBB. WO91/04014 describes a liposome delivery system in which an active agent can be encapsulated/embedded and in which molecules that are normally transported across the BBB (e.g., insulin or insulin-like growth factor I or II) are present on the liposome outer surface. Liposome delivery systems are also discussed in U.S. Pat. No. 4,704,355.

Polymer Delivery/Therapeutics

The agents may further be delivered attached to polymers. Polymer based therapeutics have been proposed to be effective delivery systems, and generally comprise one or more agents to be delivered attached to a polymeric molecule, which acts as a carrier. The agents are thus disposed on the polymer backbone, and are carried into the target cell together with the polymer.

The agents may be coupled, fused, mixed, combined, or otherwise joined to a polymer. The coupling, etc. between the agent and the polymer may be permanent or transient, and may involve covalent or non-covalent interactions (including ionic interactions, hydrophobic forces, Van der Waals interactions, etc.). The exact mode of coupling is not important as long as the agent is taken into a target cell substantially together with the polymer. For simplicity, the entity comprising the agent attached to the polymer carrier is referred to here as a "polymer-agent conjugate".

Any suitable polymer, for example, a natural or synthetic polymer, may be used, e.g., the carrier polymer is a synthetic polymer such as PEG. In some embodiments, the carrier polymer is a biologically inert molecule. Particular examples of polymers include polyethylene glycol (PEG), N-(2-hydroxypropyl) methacrylamide (HPMA) copolymers, polyamidoamine (PAMAM) dendrimers, HEMA, linear polyamidoamine polymers, etc. Any suitable linker for attaching the agent to the polymer may be used. In some embodiments, the linker is a biodegradable linker. Use of biodegradable linkers enables controlled release of the agent on exposure to the extracellular or intracellular environment. High molecular weight macromolecules are unable to diffuse passively into cells and are instead engulfed as membrane-encircled vesicles. Once inside the vesicle, intracellular enzymes may act on the polymer-agent conjugate to effect release of the agent. Controlled intracellular release circumvents the toxic side effects associated with many drugs.

Furthermore, agents may be conjugated, attached, etc. by methods known in the art to any suitable polymer and delivered. The agents may in particular comprise any of the molecules referred to as "second agents", such as polypeptides, nucleic acids, macromolecules, etc., as described in the section below. In particular, the agent may comprise a pro-drug as described elsewhere.

The ability to choose the starting polymer enables the engineering of polymer-agent conjugates for desirable properties. The molecular weight of the polymer (and thus the polymer-agent conjugate), as well as its charge and hydrophobicity properties, may be precisely tailored. Advantages of using polymer-agent conjugates include economy of manufacture, stability (longer shelf life), and reduction of immunogenicity and side effects. Furthermore, polymer-agent conjugates are especially useful for the targeting of tumor cells because of the enhanced permeability and retention (EPR) effect, in which growing tumors are more "leaky" to circulating macromolecules and large particulates, allowing them easy access to the interior of the tumor. Increased accumulation and low toxicity (typically 10-20% of the toxicity of the free agent) are also observed. Use of hyperbranched dendrimers, for example, PAMAM dendrimers, is particularly advantageous in that they enable monodisperse compositions to be made and also flexibility of attachment sites (within the interior or the exterior of the dendrimer). The pH responsiveness of polymer-agent conjugates, for example, those conjugated to polyamindoamine polymers, may be tailored for particular intracellular environments. This enables the drug to be released only when the polymer therapeutic encounters a particular pH or range of pH, e.g., within a particular intracellular compartment. The polymer agent conjugates may further comprise a targeting means, such as an immunoglobulin or antibody, which directs the polymer-agent conjugate to certain tissues, organs or cells comprising a target, for example, a particular antigen. Other targeting means are described elsewhere in this document, and are also known in the art.

Particular examples of polymer-agent conjugates include "Smancs", comprising a conjugate of styrene-co-maleic anhydride and the antitumour protein neocarzinostatin, and a conjugate of PEG (polyethylene glycol) with L-asparaginase for treatment of leukaemia; PK1 (a conjugate of a HPMA copolymer with the anticancer drug doxorubicin); PK2 (similar to PK1, but furthermore including a galactose group for targeting primary and secondary liver cancer); a conjugate of HPMA copolymer with the anticancer agent captothecin; a conjugate of HPMA copolymer with the anticancer agent paclitaxel; HPMA copolymer-platinate, etc. Any of these polymer-agent conjugates are suitable for co-loading into the transgenic cells of the present technology.

Dose Levels

Typically, a physician will determine the actual dosage which will be most suitable for an individual subject. The specific dose level and frequency of dosage for any particular patient may be varied and will depend upon a variety of factors including the activity of the specific compound employed; the metabolic stability and length of action of that compound; the age, body weight, general health, sex, diet, mode and time of administration; rate of excretion; drug combination; the severity of the particular condition; and the individual undergoing therapy. The agent and/or the pharmaceutical composition of the present technology may be administered in accordance with a regimen of from 1 to 10 times per day, such as once or twice per day. For oral and parenteral administration to human patients, the daily dosage level of the agent may be in single or divided doses.

Depending upon the need, the agent may be administered at a dose of from 0.01 to 30 mg/kg body weight, such as from 0.1 to 10 mg/kg or from 0.1 to 1 mg/kg body weight. Naturally, the dosages mentioned herein are exemplary of the average case. There can, of course, be individual instances where higher or lower dosage ranges are merited.

Therapeutically Effective Amount

"Therapeutically effective amount" refers to the amount of the therapeutic agent that is effective to achieve its intended purpose. While individual patient needs may vary, determination of optimal ranges for effective amounts of the compounds related to the technology is within the skill of the art. Generally, the dosage regimen for treating a condition with the compounds and/or compositions of this technology is selected in accordance with a variety of factors, including the type, age, weight, sex, diet and medical condition of the patient; the severity of the dysfunction; the route of administration; pharmacological considerations such as the activity, efficacy, pharmacokinetic and toxicology profiles of the particular compound used; whether a drug delivery system is used; and whether the compound is administered as part of a drug combination and can be adjusted by one skilled in the art. Thus, the dosage regimen actually employed may vary widely and therefore may deviate from the exemplary dosage regimens set forth herein.

Pharmaceutical Combinations

In general, the agent may be used in combination with one or more other pharmaceutically active agents. Other agents are sometimes referred to auxiliary agents.

Pharmaceutically Acceptable Salt

The agent may be in the form of, and/or may be administered as, a pharmaceutically acceptable salt, e.g., an acid addition salt or a base salt, or a solvate thereof, including a hydrate thereof. For a review on suitable salts see Berge et al, J. (1977) *Pharm. Sci.* 66: 1-19.

Typically, a pharmaceutically acceptable salt may be readily prepared by using a desired acid or base, as appropriate. The salt may precipitate from solution and be collected by filtration or may be recovered by evaporation of the solvent.

Suitable acid addition salts are formed from acids that form non-toxic salts such as hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate, and pamoate salts.

Suitable base salts are formed from bases that form non-toxic salts and examples are sodium, potassium, aluminum, calcium, magnesium, zinc, and diethanolamine salts.

Disease States

The present technology relates to the use of a compound according to embodiments of the technology for the manufacture of a medicament for the treatment and/or prevention of a condition selected from syndrome X, obesity, hypertension, fatty liver, diabetes, hyperglycaemia, hyperinsulinemia, and stenosis.

In some embodiments, the present technology provides use of a compound according to the technology for the manufacture of a medicament for lowering concentration of cholesterol and triglycerides in the blood of mammals and/or inhibiting the oxidative modification of low density lipoprotein.

In some embodiments, the present technology provides a method for producing weigh loss or a reduction of the fat mass in a human or non-human animal in need thereof, comprising administering thereto an effective amount of a compound of the technology or a pharmaceutically acceptable salt thereof.

In some embodiments, the present technology provides a method for the modification of the fat distribution and content of animals in order to improve the quality of the meat, or product such as milk and eggs, comprising administering thereto an effective amount of a compound of the technology or a pharmaceutically acceptable salt thereof. Preferably said animal is an agricultural animal, such as gallinaceous birds, bovine, ovine, caprine or porcine mammals. The animal may be a fish or shellfish, such as salmon, cod, Tilapia, clams, oysters, lobster or crabs.

In some embodiments, the present technology provides use of a compound according to the technology or a pharmaceutically acceptable salt thereof in the manufacture of a medicament for the inhibition and/or prevention of the growth of tumors.

In some embodiments, the present technology provides use of a compound according to the technology in the manufacture of a medicament for the inhibition and/or prevention of the invasion of a primary tumor into the connective tissue.

In some embodiments, the present technology provides use of a compound according to the technology for the manufacture of a medicament for the inhibition and/or prevention of the metastatic properties of a tumor, e.g., to inhibit the formation of secondary tumors. For example, the use of the present compounds may increase the overall survival of mammals with tumors.

In some embodiments, the present technology provides a method for the treatment and/or inhibition of primary and secondary metastatic neoplasms, comprising administering a compound of the technology or a pharmaceutically acceptable salt thereof.

In some embodiments, the present technology provides use of a compound of the technology or a pharmaceutically acceptable salt thereof in the manufacture of a medicament for the prevention and/or treatment of proliferative skin disorders such as psoriasis, atopic dermatitis, non-specific dermatitis, primary irritant contact dermatitis, allergic contact dermatitis, lamellar ichthyosis, epidermolytic hyperkeratosis, pre malignant sun induced keratosis, and seborrhea.

In some embodiments, the present technology provides use of a compound of the technology or a pharmaceutically acceptable salt thereof in the manufacture of a medicament for the inhibition of proliferation and/or induction of differentiation of keratinocytes.

In some embodiments, the present technology provides use of a compound of the technology or a pharmaceutically acceptable salt thereof in the manufacture of a medicament for the prevention and/or treatment of inflammatory disorders. For example, in some embodiments, the present technology provides use of a compound of the technology or a pharmaceutically acceptable salt thereof in the manufacture of a medicament for the prevention and/or treatment of inflammatory disorders, wherein the inflammatory disorder is selected from the group comprising immune mediated disorders such as rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegeners granulomatosis), inflammatory bowel diseases and colitis (e.g., Crohn's colitis), nephritis, various inflammatory skin disorders (e.g. psoriasis, atopic dermatitis and food allergy) and acute and chronic allograft rejection after organ transplantation.

In some embodiments, the present technology provides a method for enhancing the endogenous production of interleukin-10 (IL-10) in mammalian cells or tissues, comprising administering a compound of the technology or a pharmaceutically acceptable salt thereof. In some embodiments, the mammal has developed or is susceptible to develop an autoimmune and/or inflammatory disorder.

In some embodiments, the present technology provides a method for suppression of the endogenous production of interleukin-2 (IL-2) in mammalian cells or tissues, comprising administering a compound of the technology or a pharmaceutically acceptable salt thereof. In some embodiments, the mammal has developed or is susceptible to develop an autoimmune and/or inflammatory disorder.

In some embodiments, the present technology provides use of a compound of the technology or a pharmaceutically acceptable salt thereof in the manufacture of a medicament for the inhibition of proliferation of stimulated peripheral mononuclear cells (PBMC).

Further description of these and other diseases is provided below.

Obesity and Related Diseases

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, Acanthosis nigricans, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease.

In some embodiments, the present technology provides a treatment regimen that is useful in returning the body weight of obese subjects toward a normal body weight. In some embodiments, the technology provides a therapy for obesity that results in maintenance of the lowered body weight for an extended period of time. Further, in some embodiments the present technology reduces or inhibits the weight gain normally induced by fat rich diets.

In some embodiments, the present technology prevents obesity and, once treatment has begun, to arrests progression or prevents the onset of diseases that are the consequence of, or secondary to, the obesity, such as hypertension and fatty liver.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficiency, normal variant short stature, Turner's syndrome, and other pathological conditions showing reduced metabolic activity.

In some embodiments, the present technology provides a treatment regimen that is useful in lowering the blood pressure. Further, in some embodiments the present technology provides a treatment regimen that is useful in lowering the concentration of triacylglycerols in the liver. It is anticipated that such a regimen provides an inhibiting effect on the development of a fatty liver condition and is suited as a method for the treatment of the manifested disease.

In some embodiments, the compounds of the present technology activate the oxidation, and also reduce the concentration, of triglycerides in the liver.

The term "metabolic syndrome" is used to describe a multimetabolic syndrome that is inter alia characterized by hyperinsulinemia, insulin resistance, obesity, glucose intolerance, Type 2 diabetes mellitus, dyslipidemia, or hypertension.

As indicated above it is anticipated that the compounds of the present technology provide a positive effect on all the conditions mentioned above, e.g., by regulating both glucose and lipid homeostasis, and thus it is anticipated that the compounds of the present technology are suitable agents for the regulation of the above defined metabolic disease (sometimes called syndrome X).

Diabetes

There are two major forms of diabetes mellitus. One is type I diabetes, which is also known as insulin-dependent diabetes mellitus (IDDM), and the other is type II diabetes, which is also known as noninsulin-dependent diabetes mellitus (NIDDM). Most patients with IDDM have a common pathological picture; the nearly total disappearance of insulin-producing pancreatic beta cells which results in hyperglycemia.

Considerable evidence has been accumulated showing that most IDDM is the consequence of progressive beta-cell destruction during an asymptomatic period often extending over many years. The prediabetic period is recognized usually by the detection of circulating islet-cell autoantibodies and insulin autoantibodies.

As such, there is a need for a compound that is nontoxic and has no or minimal side effects but that would prevent clinical IDDM and NIDDM.

Type I diabetes: severe diabetes mellitus, usually of abrupt onset prior to maturity, characterized by low plasma insulin levels, polydipsia, polyuria, increased appetite, weight loss and episodic ketoacidosis; also referred to as IDDM.

Type II diabetes: an often mild form of diabetes mellitus, often of gradual onset, usually in adults, characterized by normal to high absolute plasma insulin levels which are relatively low in relation to plasma glucose levels; also referred to as NIDDM.

Type I and II diabetes are in accordance with an etiologic classification considered as primary diabetes respectively.

Secondary diabetes comprises pancreatic, extrapancreatic and/or endocrine or drug-induced diabetes. Further, some types of diabetes are classified as exceptional forms. These include lipoatrophic, myatonic diabetes, and a type of diabetes caused by disturbance of insulin receptors.

Considering the high prevalence of diabetes in our society and the serious consequences associated therewith as discussed above, any therapeutic drug potentially useful for the treatment and prevention of this disease would have a profound beneficial effect on their health. There is a need in the art for a drug that reduces the concentration of glucose in the blood of diabetic subjects without significant adverse side effects.

Accordingly, in some embodiments, the present technology provides a treatment regimen that is useful in lowering the blood glucose and to treat a diabetic condition. Moreover, in some embodiments, the present technology provides a treatment regimen that is useful in lowering the concentration of insulin in the blood, and to increase the effect of the remaining insulin.

Stenosis

Many pathological conditions have been found to be associated with smooth muscle cell proliferation. Such conditions include restenosis, arteriosclerosis, coronary heart disease, thrombosis, myocardial infarction, stroke, smooth muscle neoplasms such as leiomyoma, and leiomyosarcoma of the bowel and uterus and uterine fibroid or fibroma.

Over half a million interventional intravascular procedures are performed each year. While such invasive procedures continue to improve over time, as many as 30% to 50% of the procedures performed each year fail as a result of restenosis, e.g., the formation of secondary stenosis. The reduction of restenosis is, therefore, often cited as the most critical factor in increasing the success realized in the treatment of cardiovascular disease through the use of interventional intravascular procedures, such as angioplasty, atherectomy, and procedures utilizing stents, and laser technology.

In balloon angioplasty, e.g. Percutaneous Transluminal Coronary Angioplasty (PTCA), a small incision is made to an artery in the patient's leg or arm and a long hollow tube, called a guide catheter, is inserted into the artery. A thick guide wire and deflated balloon catheter are then inserted into the guide catheter and are carefully advanced through the patient's blood vessels using X-ray visualization. The deflated balloon is advanced until it reaches the site of the luminal narrowing, at which point the physician inflates the balloon one or more times to a pressure of about 4-6 atm for about 60 seconds. When inflated, the balloon cracks and fractures the plaque and stretches the muscle fiber in the artery wall beyond its ability to recoil completely. Although no plaque is removed in this procedure, the fracturing of the plaque and the stretching of the arterial wall increase the vessel lumen, thereby allowing for increased blood flow.

The restenosis that accompanies such procedures is characterized by platelet aggregation and adhesion, smooth muscle cell proliferation, narrowing of the vessel lumen, restricted vasodilatation, and an increase in blood pressure. Smooth muscle cells in the intimal layer of the artery have been reported to enter the growth cycle within about 2-3 days of these procedures and to proliferate for several days thereafter (intimal hyperplasia).

Compounds that reportedly suppress smooth muscle proliferation in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation.

As is apparent from the foregoing, many problems remain to be solved in the use of inhibitory drugs to effectively treat smooth muscle cell mobilization and proliferation. It would be highly advantageous to develop new compositions or methods for inhibiting stenosis, restenosis or related disorders due to proliferation and mobilization of vascular smooth muscle cells following, for example, traumatic injury to vessels rendered during vascular surgery.

Accordingly, it is anticipated that embodiments of compounds in accordance with the present technology are effective in the treatment of these diseases.

Tumors

As discussed in WO 02/03983, the development of new and more effective chemotherapeutic agents for cancer treatment requires considering a variety of factors including cytotoxicity, tumor cell proliferation, invasion, and metastasis. Conventional anticancer agents have typically been identified on the basis of their cytotoxicity alone.

Tumor progression is thought to occur when variant cells having selective growth properties arise within a tumor cell population, and one of the final stages of tumor progression is the appearance of the metastatic phenotype.

During metastasis, the tumor cells invade the blood vessels, survive against circulating host immune defenses, and then extravasate, implant, and grow at sites distant from the primary tumor. This ability of tumor cells to invade neighboring tissues and to colonize other organs is among the leading causes of cancer related deaths.

The term metastasis encompasses a number of phenotypic traits that together result in the clinical problem that most often leads to death from cancer. The cells lose their adherence and restrained position within an organized tissue, move into adjacent sites, develop the capacity both to invade and to egress from blood vessels, and become capable of proliferating in unnatural locations or environments. These changes in growth patterns are accompanied by an accumulation of biochemical alterations that have the capacity to promote the metastatic process.

So far, little is known about the intrinsic mechanism involved in the metastatic cascade. It is likely that in some cases the augmented metastatic potential of certain tumor cells may be due to an increased expression of oncogenes, which normally are responsible for control of various cellular functions, including differentiation, proliferation, cell motility, and communication. Further, it has been shown that substances that modulate signal transduction pathways can inhibit the metastatic behavior of a tumor, and it is also speculated that compounds with surface related effects, e.g., compounds that modulates the cell membranes, might be involved in the process leading to metastasis.

Cancer is a disease of inappropriate tissue accumulation. This derangement is most evident clinically when tumor tissue bulk compromises the function of vital organs. Contrary to what is generally thought, human malignant disorders are usually not diseases of rapid cell proliferation. In fact, the cells of most common cancers proliferate more slowly than many cells in normal tissues. It is a relatively slow accumulation of tumor tissue within vital organs that proves fatal to most patients who die of cancer.

Chemotherapeutic agents share one characteristic: they are usually more effective in killing or damaging malignant cells than normal cells. However, the fact that they do harm normal cells indicates their potential for toxicity. Nearly all chemotherapeutic agents currently in use interfere with DNA synthesis, with the provision of precursors for DNA and RNA synthesis, or with mitosis. Such drugs are most effective against cycling cells. The mechanism of cell death after treatment with any single agent or combination of agents is complex and is likely to include more than one process. Because most clinically detectable tumors are composed mostly of non-cycling cells, it is not surprising that chemotherapy is not always effective in eradicating cancer.

The strategy of cancer treatment is to shift tumor cells from a non-cycling compartment to a cycling compartment. Several methods that promote this shift form the basis for combined-modality treatment. Surgery is most commonly used to reduce tumor size and thus facilitate re-entry of cancer cells into the cell cycle. After the primary tumor is completely removed, microscopic metastases may remain at distant sites. Because of their small size, the micrometastases are composed principally of cycling cells. Small numbers of cells that remain at primary tumor site are also likely to re-enter the cell cycle. Thus, the remaining cancer cells are often susceptible to chemotherapy. Radiation therapy or chemotherapy alone can also be used to reduce tumor bulk and thus recruit cells into the cycling cell compartment.

Combination drug therapy is, therefore, the basis for most chemotherapy employed at present. Combination chemotherapy uses the different mechanisms of action and cytotoxic potentials of multiple drugs. However, even though the chemotherapeutic agents are more effective in killing or damaging malignant cells than normal cells, the fact that they do harm normal cells indicates their great potential for toxicity. For chemotherapy to be effective, the patient must be in good physiologic condition.

Cancer treatment requires inhibition of a variety of factors including tumor cell proliferation, metastatic dissemination of cancer cells to other parts of the body, invasion, tumor-induced neovascularization, and enhancement of host immunological responses and cytotoxicity.

Conventional cancer chemotherapeutic agents have often been selected on the basis of their cytotoxicity to tumor cells. However, some anticancer agents have adverse effects on the patient's immunological system. Unfortunately, for the vast majority of conventional antineoplastic agents the margin between an effective dose and a toxic dose, e.g., the therapeutic index, is extremely low. Thus, it would be greatly advantageous if a cancer therapy or treatment could be developed that would afford noncytotoxic protection against factors that might lead to growth, progression and metastasis of invasive cancers.

Accordingly, in some embodiments, the present technology provides a method for the prevention and/or treatment of primary and metastatic neoplasms that involves using a fatty acid analogue, or a lipid comprising a fatty acid analogue, of the present technology to treat a patient suffering from a cancer.

The two essential features of cancer are invasion and metastasis. At one extreme, microinvasion of the basement membrane characterizes the transition from neoplasia to cancer, and at the other extreme, metastases generally lead to death. Invasion into the underlying connective tissue by primary tumor proceeds in stages and is facilitated by various mediators produced by the tumor cells. Tumor cells that have not invaded the basement membrane and remain confined within the epithelium are termed carcinoma in situ. Metastases, on the other hand, may form when circulating tumor cells with adherent lymphocytes and platelets are trapped in capillaries and the tumor cell membrane interacts with the capillary endothelium. The capillary endothelial junctions retract, and tumor cell ligands bind to receptors on the endothelial and basement membranes.

Tumor cells then release collagenase IV, which destroys collagen IV, a major component of the underlying basement membrane. Invasion of the subcapillary connective tissue is aided by binding to the glycoproteins laminin and fibronectin, by the release of proteases that destroy the matrix, and by the secretion of motility and chemotactic factors. Tumor cells then may proliferate and synthesize platelet aggregatory factors such as thromboxanes and procoagulants, thereby leading to the deposition of a fibrin cocoon around the cells. Such a cocoon may protect the micrometastasis from attack by the host's immune system.

Cancers that can be prevented and/or treated by the compositions and methods of the present technology include, but are not limited to, human sarcomas and carcinomas, e.g. carcinomas, e.g., colon carcinoma, pancreatic cancer, breast cancer, ovarian cancer, prostate cancer, thyroid cancer, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Specific examples of such cancers are described in the sections below.

Skin Disorders

As discussed in WO 02/26218, proliferative skin diseases are widespread throughout the world and afflict millions of humans and their domesticated animals Proliferative skin diseases are characterized by keratinocyte cell proliferation, or division, and may also be associated with incomplete epidermal differentiation. Psoriasis is the most serious of the proliferative skin diseases with which this technology is concerned.

Psoriasis is a genetically determined disease of the skin characterized by two biological hallmarks. First, there is a profound epidermal hyperproliferation related to accelerated and incomplete differentiation. Second, there is a marked inflammation of both epidermis and dermis with an increased recruitment of T lymphocytes, and in some cases, formation of neutrophil microabcesses. Many pathologic features of psoriasis can be attributed to alterations in the growth and maturation of epidermal keratinocytes, with increased proliferation of epidermal cells, occurring within 0.2 mm of the skin's surface.

Traditional investigations into the pathogenesis of psoriasis have focused on the increased proliferation and hyperplasia of the epidermis. In normal skin, the time for a cell to move from the basal layer through the granular layer is 4 to 5 weeks. In psoriatic lesions, the time is decreased sevenfold to tenfold because of a shortened cell cycle time, an increase in the absolute number of cells capable of proliferating, and an increased proportion of cells that are actually dividing. The hyperproliferative phenomenon is also expressed, although to a substantially smaller degree, in the clinically uninvolved skin of psoriatic patients.

A common form of psoriasis, psoriasis vulgaris, is characterized by well-demarcated erythematous plaques covered by thick, silvery scales. A characteristic finding is the isomorphic response (Koebner phenomenon), in which new psoriatic lesions arise at sites of cutaneous trauma. Lesions are often localized to the extensor surfaces of the extremities, and the nails and scalp are also commonly involved.

Therapeutic efforts in psoriasis are aimed at decreasing the proliferative rate of the epidermis, either by direct action on cell division or indirectly by reducing the immunological response. For patients with localized, limited psoriasis, administration of topical corticosteroids is the most convenient outpatient therapy.

Rapid improvement may be seen with this approach, but the beneficial short-term efficacy is limited and chronic topical corticosteroid treatment is not advisable. Side effects from chronic topical corticosteroid therapy can include atrophy of the skin, development of tolerance to the agent used (tachyphylaxis), and serious exacerbation of the disease after discontinuation. Pituitary-adrenal suppression is a potential and serious complication of potent topical corticosteroid therapy, particularly when the agent covers a large portion of the body surface and is used under occlusive dressings.

The retinoids, particularly etretinate, either alone or in combination with PUVA, are also an effective treatment for psoriasis. Etretinate is especially useful in the exfoliative and pustular varieties of psoriasis. However, several major potential complications must be monitored in patients placed on retinoids. As a class, the retinoids are potent teratogens and should not be given to women of childbearing age who are not using adequate contraception.

Etretinate, like other retinoids, can produce elevations in cholesterol and triglyceride levels; therefore dietary regulation may be necessary. In addition, because etretinate can induce hepatotoxicity, liver function tests should be performed before and at regular intervals during use of the drug.

Considering the complications and side effects attendant to the use of different drugs and photochemotherapy currently used in treating a skin proliferative disease such as psoriasis, there is a need for a new method and a new composition to inhibit keratinocyte proliferation to alleviate the symptoms of skin proliferation diseases.

Inflammatory and Auto-Immune Disorders

As discussed in WO 02/43728, interleukins, interferons, colony stimulating factors and TNF-alpha are examples of a group of diverse multi-functional proteins called cytokines. Cytokines are a class of secreted soluble proteins normally present in very low concentration in a variety of cells. Lymphoid, inflammatory hemopoietic, and other cells such as connective tissue cells (e.g. fibroblasts, osteoblasts) secrete a variety of cytokines which regulate the immune, inflammatory, repair, and acute phase responses by controlling cell proliferation, differentiation, and effector functions. The effects of cytokines are mediated through binding to high affinity receptors on specific cell types.

An important cytokine is IL-10, a 35-40 kDa peptide produced by helper T-cells, B-cells, monocytes, macrophages, and other cell types. In vitro, IL-10 has demonstrated immunosuppressive properties as evidenced by its ability to suppress cytokine production including IL-1 and TNFa. IL-10 also inhibits activation of other inflammatory cytokines, and therefore has potent anti-inflammatory activity.

It has been of recent interest to administer-IL-10 in the treatment of certain conditions characterized by excessive IL-1 and TNF-alpha production. Such diseases or conditions include loosening of prosthetic joint implants, inflammation, diabetes, cancer, graft versus host diseases, viral, fungal and bacterial infections, lipopolysaccharide endotoxin shock, diseases of depressed bone marrow function, thrombocytopenia, osteoporosis, spondyloarthropathies, Paget's disease, inflammatory bowel disease, arthritis, osteoarthritis, autoimmune diseases such as rheumatoid arthritis, systemic lupus erythematosus, and connective tissue diseases.

For example, purified IL-10 has been shown in vitro to suppress certain types of viral infections. U.S. Pat. No. 5,665,345 discloses a method for inhibiting replication of the human immunodeficiency virus, retro-viruses, and Kaposi sarcoma in human cells by administering IL-10.

IL-10 has also been suggested for use in the treatment of certain cancers. U.S. Pat. No. 5,570,190 discloses administering exogenous IL-10 to treat mammals suffering from acute myelogenous leukemia and acute lymphocytic leukemia. IL-10 is said to be administered either in the purified or recombinant form and is believed to inhibit the proliferation of acute leukemia blast cells. Similarly, IL-10 was shown to inhibit bone marrow metastasis in severe combined immunodeficient mice.

The above conventional approaches to treating conditions characterized by excessive IL-1 and TNF-alpha production have been limited to administering exogenous purified or recombinant IL-10 intravenously. Since IL-10 is a protein, it is difficult to infuse intravenously into a mammal because proteins often leach out of solution and bind to the plastic or glass used in intravenous administration sets. Also, proteins are often incompatible and precipitate when mixed with physiological solutions such as dextrose or saline. In addition, oral and topical routes are unavailable for IL-10 administration. The oral route is unavailable because protein is degraded in the gastrointestinal tract. None of the above approaches suggests enhancing endogenous IL-10 production in mammals for prophylaxis and treatment of diseases or conditions.

Further, it is known that IL-10 is a powerful deactivator of macrophages and T cells, and inadequate production has been implicated in various autoimmune and inflammatory disorders.

As shown in U.S. Pat. No. 8,178,713, embodiments of the compounds provided herein enhance both LPS and PHA stimulated IL-10, and suppress PHA stimulated IL-2 production in PBMC from healthy blood donors. These findings suggested a marked anti-inflammatory net effect of the present compounds by both enhancing the release of the anti-inflammatory cytokine IL-10 and by suppressing the release of the inflammatory cytokine IL-2. Second, the findings suggested that the present compounds may modulate both monocyte (e.g., LPS stimulation) and lymphocyte activation (e.g., PHA stimulation). Finally, the in vitro effect of the present compounds on activated PBMC from healthy blood donors may reflect the situation in various patient populations characterized by enhanced inflammatory activation in vivo. In fact, ex vivo activated PBMC from healthy controls, may represent the relevant target cells for therapeutically intervention in vivo in various inflammatory disorders.

In addition, or in the alternative, embodiments of the compound or composition of the present technology are useful in the treatment of the disorders listed in WO/1998/05635. For ease of reference, part of that list is now provided: cancer, inflammation or inflammatory disease, dermatological disorders, fever, cardiovascular effects, hemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumor growth, invasion and spread, angiogenesis, metastases, malignant, ascites and malignant pleural effusion; cerebral ischemia, ischemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, embodiments of the compound or composition of the present technology are useful in the treatment of disorders listed in WO/1998/07859. For ease of reference, part of that list is now provided: cytokine and cell proliferation/differentiation activity; immunosuppressant or immunostimulant activity (e.g., for treating immune deficiency, including infection with human immune deficiency virus; regulation of lymphocyte growth; treating cancer and many autoimmune diseases, and to prevent transplant rejection or induce tumor immunity); regulation of hematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilizing specific cell types to sites of injury or infection); hemostatic and thrombolytic activity (e.g. for treating hemophilia and stroke); anti-inflammatory activity (for treating e.g. septic shock or Crohn's disease); as antimicrobials; modulators of e.g. metabolism or behavior; as analgesics; treating specific deficiency disorders; in treatment of e.g. psoriasis, in human or veterinary medicine.

In addition, or in the alternative, embodiments of the composition of the present technology are useful in the treatment of disorders listed in WO/1998/09985. For ease of reference, part of that list is now provided: macrophage inhibitory and/or T cell inhibitory activity and thus, anti-inflammatory activity; anti-immune activity, e.g., inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g., retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumor cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Treatment

Embodiments of the technology include any therapeutic application that can benefit a human or non-human animal, for example a mammal. As such, both human and veterinary treatments are within the scope of the present technology.

Treatment may be in respect of an existing condition or it may be prophylactic. It may be of an adult, a juvenile, an infant, a fetus, or a part of any of the aforesaid (e.g., an organ, tissue, cell, or nucleic acid molecule).

In some embodiments, an active agent for use in treatment is administered via any appropriate route and at any appropriate dosage. Dosages can vary between wide limits, depending upon the nature of the treatment, the age and condition of the individual to be treated, etc., and a physician will ultimately determine appropriate dosages to be used. However, without being bound by any particular dosages, a daily dosage of a compound of the present technology of from 1 μg to 1 mg/kg body weight may be suitable. The dosage may be repeated as often as appropriate. If side effects develop, the amount and/or frequency of the dosage can be reduced, in accordance with good clinical practice.

Polymorphic Form(s) and/or Asymmetric Carbon(s)

Embodiments of compounds according to the present technology may exist in a polymorphic form. In addition, embodiments of compounds according to the present technology may contain one or more asymmetric carbon atoms and therefore exist in two or more stereoisomeric forms. Where an agent contains an alkenyl or alkenylene group, cis (E) and trans (Z) isomerism may also occur. The present technology includes the individual stereoisomers of the agent and, where appropriate, the individual tautomeric forms thereof, together with mixtures thereof.

Separation of diastereoisomers and/or cis and trans isomers may be achieved by conventional techniques, e.g., by fractional crystallization, chromatography, or H.P.L.C. of a stereoisomeric mixture of the agent or a suitable salt or derivative thereof. An individual enantiomer of a compound of the agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Isotopic Variations

The present technology also includes all suitable isotopic variations of the agent or a pharmaceutically acceptable salt thereof. An isotopic variation of an agent of the present technology or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulfur, fluorine and chlorine such as $^2$H, $^3$H, $^{13}$C, $^{15}$N, $^{17}$O, $^{18}$O, $^{31}$P, $^{32}$P, $^{35}$S, $^{35}$S, $^{18}$F, and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, e.g., $^3$H, and carbon-14, e.g., $^{14}$C, isotopes are particularly useful for their ease of preparation and detectability. Further, substitution with isotopes such as deuterium, e.g., $^2$H, may afford certain therapeutic advantages resulting from greater metabolic stability, for example, increased in vivo half-life or reduced dosage requirements and hence may be preferred in some circumstances. Isotopic variations of the agent of the present technology and pharmaceutically acceptable salts thereof of this technology can generally be prepared by conventional procedures using appropriate isotopic variations of suitable reagents.

Pro-Drug

In some embodiments, compounds according to the technology are derived from a prodrug. Prodrugs are entities that may or may not possess pharmacological activity as such, but may be administered (such as orally or parenterally) and thereafter subject to bioactivation (for example metabolized) in the body to form the agent of the present technology which is pharmacologically active. Examples of prodrugs include entities that have certain protected group(s) and that may not possess pharmacological activity as such, but may, in certain instances, be administered (such as orally or parenterally) and thereafter metabolized in the body to form the agent of the present technology that are pharmacologically active.

Pro-Moiety

In some embodiments, the technology encompasses certain moieties known as "pro-moieties", for example as described in "Design of Prodrugs" by H. Bundgaard, Elsevier, 1985 (the disclosure of which is hereby incorporated by reference). In some embodiments, a pro-moiety may be placed on appropriate functionalities of the agents. Such prodrugs are also included within the scope of the technology.

Derivative

The term "derivative" or "derivatized" as used herein includes chemical modification of an agent. Illustrative of such chemical modifications would be replacement of hydrogen by a halo group, an alkyl group, an acyl group, or an amino group.

Chemical Modification

In one embodiment of the present technology, the agent may be a chemically modified agent. The chemical modification of an agent of the present technology may either enhance or reduce hydrogen bonding interaction, charge interaction, hydrophobic interaction, Van Der Waals interaction, or dipole interaction between the agent and the target. In some embodiments, the identified agent may act as a model (for example, a template) for the development of other compounds.

Although the disclosure herein refers to certain illustrated embodiments, it is to be understood that these embodiments are presented by way of example and not by way of limitation.

Combination with Sialic Acid Analogs

In some embodiments, the lipid compositions described above (e.g., the natural lipid compositions and structured lipid compositions) may be used in combination with one or more sialic acid analogs. As used herein sialic acid analogs include sialic acids and sialic acid precursors. Preferably, sialic acids or sialic acid precursors are selected from the group consisting of n-glycolylneuraminic acid, n-acetylneuraminic acid and N-Acetyl-D-mannosamine. In some embodiments, the composition may comprise two or more of the following sialic acids: Neuraminic acid, 5-N-Acetyl-4-O-acetyl-neuraminic acid, 5-N-Acetyl-7-O-acetyl-neuraminic acid, 5-N-Acetyl-8-O-acetyl-neuraminic acid, 5-N-Acetyl-9-O-acetyl-neuraminic acid, 5-N-Acetyl-4,9-di-O-acetyl-neuraminic acid, 5-N-Acetyl-7,9-di-O-acetyl-neuraminic acid, 5-N-Acetyl-8,9-di-O-acetyl-neuraminic acid, 5-N-Acetyl-7,8,9-tri-O-acetyl-neuraminic acid, 5-N-Acetyl-9-O-L-lactyl-acetyl-neuraminic acid, 5-N-Acetyl-4-O-acetyl-9-O-lactyl-acetyl-neuraminic acid, 5-N-Acetyl-8-O-methyl-neuraminic acid, 5-N-Acetyl-9-O-acetyl-8-O-methyl-neuraminic acid, 5-N-Acetyl-8-O-sulpho-neuraminic acid, 5-N-Acetyl-9-O-phosphoro-neuraminic acid, 5-N-Acetyl-2-deoxy-2,3-didehydro-neuraminic acid, 5-N-Acetyl-9-O-acetyl-2-deoxy-2,3-didehydro-neuraminic acid, 5-N-Acetyl-2-deoxy-2,3-didehydro-9-O-lactyl-neuraminic acid, 5-N-Acetyl-2,7-anhydro-neuraminic acid, 4-O-Acetyl-5-N-glycolyl-neuraminic acid, 7-O-Acetyl-5-N-glycolyl-neuraminic acid, 8-O-Acetyl-5-N-glycolylneuraminic acid, 9-O-Acetyl-5-N-glycolyl-neuraminic acid, 7,9-Di-O-acetyl-5-N-glycolyl-neuraminic acid, 8,9-Di-O-acetyl-5-N-glycolyl-neuraminic acid, 7,8,9-Tri-O-acetyl-5-N-glycolyl-neuraminic acid, 5-N-glycolyl-9-O-lactyl-neuraminic acid, 5-N-glycolyl-8-O-methyl-neuraminic acid, 9-O-Acetyl-5-N-glycolyl-8-O-methyl-neuraminic acid, 7,9-di-O-Acetyl-5-N-glycolyl-8-O-methyl-neuraminic acid, 5-N-glycolyl-8-O-sulpho-neuraminic acid, N-(O-acetyl)glycolylneuraminic acid, N-(O-Methyl)glycolylneuraminic acid, 2-Deoxy-2,3-didehydro-5-N-glycolyl-neuraminic acid, 9-O-Acetyl-2-deoxy-2,3-didehydo-5-N-glycolyl-neuraminic acid, 2-Deoxy-2,3-didehydro-5-N-glycolyl-9-O-lactyl-neuraminic acid, 2-Deoxy-2,3-didehydro-5-N-glycolyl-8-O-methyl-neuraminic acid, 2,7-Anhydro-5-N-glycolyl-neuraminic acid, 2,7-Anhydro-5-N-glycolyl-8-O-methyl-neuraminic acid, 2-Keto-3-deoxynononic acid, and 9-O-Acetyl-2-keto-3-deoxynononic acid. In some embodiments, the compositions may comprise 2, 3, 4, 5, 6, 7, 8, 9, 10 or more sialic acid analogs. In some embodiments, the sialic acid analogs have a purity selected from the group consisting of greater than 90%, 95%, 99%, and 99.5% pure.

The sialic acid precursor may be co-formulated in the same delivery vehicle as the lipid composition, or may be provided in a separated delivery vehicle. In some embodiments, the sialic acid composition or sialic acid precursor composition is provided in a daily dosage selected from the group consisting of 1 microgram to 100 mg/day, 100 microgram to 20 mg/day, and 200 microgram to 10 mg/day. In some embodiments, the sialic acid composition or sialic acid precursor composition is provided in a daily dosage selected from the group consisting of 0.1 to 10 mg/150 kg subject/day, 0.3 to 5 mg/150 kg subject/day, and 0.5 to 2 mg/150 kg subject/day. In some embodiments, the administering is selected from the group consisting of enteral administration, parenteral administration, oral administration, sublingual administration, subcutaneous administration, intramuscular administration, and intravenous administration.

Thus, the lipid composition/sialic acid compositions may be provided in a single dosage form or a part of treatment regime where the lipid composition and sialic acid are co-administered. It is contemplated that these compositions may be utilized for the uses described above.

EXAMPLES

TTA has shown promise as an agent for the treatment of various metabolic conditions and related conditions, including metabolic syndrome, diabetes, obesity, fatty liver, and hypertension. TTA also shows promise as a nutritional supplement that can be used to reduce weight and improve body composition. See e.g., U.S. Pat. Nos. 7,902,399; 7,659,242; 7,378,443; 7,230,029; 7,026,356; 6,441,036; 6,417,232; and 6,365,628, all of which are incorporated by reference herein in their entirety.

TTA has properties very similar to natural fatty acids, the main difference being that TTA is not oxidized by the mitochondrial beta-oxidation system. However, the presence of non-beta-oxidizable fatty acid analogues has been shown to increase the beta-oxidation of other fatty acids.

For example, administration of TTA to rats for 12 weeks nearly doubled the hepatic and plasma content of monounsaturated fatty acids (mainly oleic acid), while polyunsaturated fatty acids (mainly linoleic acid and DHA) decreased. Thus TTA modifies the composition of lipids in various tissues. TTA also modifies fat content and it is anticipated that TTA also modifies fat distribution.

Feeding moderate doses of TTA to animals like rats, mice, rabbits, and dogs decreases plasma cholesterol and triacylglycerol levels within days of treatment. Tetradecylselenoacetic (TSA) has the same effects. TTA compounds with sulfur substituted in positions 5 or 7 increase beta-oxidation of other lipids and it is thus anticipated that also fatty acid analogous such as TTA lower plasma levels of triglycerides and cholesterol. TTA and TSA are far more potent in this respect than polyunsaturated fatty acids like EPA.

An important mechanism of action of 3-thia fatty acids is a significant increase in mitochondrial fatty acid oxidation, which reduces the availability of fatty acids for esterification. The synthesis of triacylglycerol and cholesterol is reduced and the secretion of VLDL from the liver is decreased. This has the effect of reducing the production of LDL. All these effects seem to be at least partly mediated by peroxisome proliferator activated receptors (PPAR), ubiquitous transcription factors involved in the regulation of lipid metabolism.

Example 1—Improved Synthesis of TTA

As such, the benefits of non-beta-oxidizable fa acid analogues such as TTA and TSA are many. However, TTA compositions that have been marketed in the United States and Europe for human consumption have been associated with side effects, including lethargy, muscle cramps and muscle pain. It is likely that these side effects are due to contaminants in the commercially produced TTA. Accordingly, during the development of embodiments of the technology, experiments were performed to provide a synthesis of TTA that has reduced side effects and to test the use of such TTA compositions in human nutrition.

1-bromotetradecane (Aldrich 195332) and thioglycolic acid (Fluka 88650) were obtained from Sigma-Aldrich. In some embodiments, a method for the synthesis of TTA comprises distillation of bromotetradecane-1 to provide a reagent for the synthesis. In particular, a mass of 29.5 kg of commercial bromotetradecane-1 was distilled in two steps at 79° C. under reduced pressure; the two distillates were combined and totaled 25.0 kg. A dark residue of 2.7 kg was removed.

Then, to synthesize TTA, 7.6 kg NaOH was carefully dissolved in 126.7 kg of methanol while stirring at room temperature. Then a mass of 9.2 kg of thioglycolic acid was weighed in a protective layer of about 2.5 kg of methanol and transferred to the reactor while stirring. Subsequently, 25.0 kg of the distilled 1-bromotetradecane preparation under a protective layer of 2.5 kg of methanol was slowly transferred (e.g., over a time of about a half hour to avoid clumping) to the reactor while stirring. Heating started when about half the amount of bromtetradecane-1 was added. The mixture was stirred under reflux conditions in the reactor at about 65° C. for about 20 hours. After cooling to approximately 55 to 60° C., 50 kg of citric acid dissolved in about 75 kg of hot water were added under heavy stirring. The temperature was kept at approximately 50 to 60° C. Quick addition of late and fast phase separation to limit the formation of methyl was utilized.

Stirring was stopped and the bottom water was drained off as quickly as possible after phase separation. The temperature in the oil phase was increased to 85 to 90° C. during stirring and the composition was kept under vacuum to reduce the amount of methanol. The oil phase was washed 6 times with 30-50 liters of hot water containing about 2 kg of citric acid each time. After washing, fatty acids were dried at 85 to 90° C. under vacuum. The yield was 20 kg.

Crystallization: The liquid TTA (20 kg) was mixed at approximately 70° C. with 100 of kg room-temperature acetone. After cooling to 30 to 35° C. 145 kg of fresh acetone were added to the mix to provide a total of 245 kg acetone added. The mixture was then cooled to −30° C. and filtered. After drainage of the liquid, the crystal phase was dried under vacuum and heated to about 40° C. The yield was 19.9 kg.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

I claim:

1. A method for producing lipids comprising tetradecylthioacetic acid (TTA) and omega-3 fatty acids, the method comprising:
   1) providing TTA to algae in vitro; and
   2) isolating lipids comprising TTA and omega-3 fatty acid moieties from the algae, wherein said lipids are phospholipids or triglycerides to which the TTA and omega-3 fatty acid moieties are esterified.

2. The method of claim 1, further comprising combining the lipids comprising TTA with lipids isolated from a marine organism.

3. The method of claim 1, wherein the algae is in a culture.

4. The method of claim 1, wherein the TTA is produced by reacting thioglycolic acid with bromotetradecane.

5. The method of claim 1, wherein the TTA is produced by a method comprising dissolving sodium hydroxide in methanol to produce a reaction solution, adding thioglycolic acid to the reaction solution, adding 1-bromotetradecane to the reaction solution, adding citric acid to the reaction solution, and isolating TTA from the reaction solution.

6. The method of claim 1, wherein the lipids comprising TTA include phospholipids.

7. The method of claim 1, wherein the lipid comprises a phosphatidylcholine, phosphatidylethanolamine, phosphatidylserine, phosphatidylglycerol, or phosphatidylinositol headgroup.

8. The method of claim 1, wherein said omega-3 fatty acid moiety is selected from the group consisting of EPA and DHA.

9. The method of claim 1, further comprising encapsulating the lipids comprising TTA.

* * * * *